United States Patent
Adachi et al.

(10) Patent No.: US 9,634,262 B2
(45) Date of Patent: Apr. 25, 2017

(54) CHARGE TRANSPORT MATERIAL, HOST MATERIAL, THIN FILM AND ORGANIC LIGHT EMITTING ELEMENT

(71) Applicant: KYUSHU UNIVERSITY NATIONAL UNIVERSITY CORPORATION, Fukuoka-shi, Fukuoka (JP)

(72) Inventors: Chihaya Adachi, Fukuoka (JP); Takuma Yasuda, Fukuoka (JP); Takuro Nishimoto, Fukuoka (JP); Saeyoun Lee, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 0 days.

(21) Appl. No.: 14/772,802

(22) PCT Filed: Mar. 4, 2014

(86) PCT No.: PCT/JP2014/055427
§ 371 (c)(1),
(2) Date: Sep. 4, 2015

(87) PCT Pub. No.: WO2014/136758
PCT Pub. Date: Sep. 12, 2014

(65) Prior Publication Data
US 2016/0020409 A1   Jan. 21, 2016

(30) Foreign Application Priority Data
Mar. 5, 2013 (JP) .................................. 2013-043533

(51) Int. Cl.
C09K 11/06 (2006.01)
H01L 51/00 (2006.01)
C07F 9/6593 (2006.01)
C09K 11/02 (2006.01)
H01L 51/50 (2006.01)

(52) U.S. Cl.
CPC ...... *H01L 51/0072* (2013.01); *C07F 9/65815* (2013.01); *C09K 11/025* (2013.01); *C09K 11/06* (2013.01); *H01L 51/0061* (2013.01); *H01L 51/0069* (2013.01); *C09K 2211/1007* (2013.01); *C09K 2211/1029* (2013.01); *H01L 51/0071* (2013.01); *H01L 51/0074* (2013.01); *H01L 51/5012* (2013.01); *H01L 51/5024* (2013.01)

(58) Field of Classification Search
CPC ............. H01L 51/0072; H01L 51/0071; H01L 51/0061; C07F 9/65815; C09K 11/06
See application file for complete search history.

(56) References Cited

U.S. PATENT DOCUMENTS 8,859,110 B2   10/2014   Fuchs et al.

FOREIGN PATENT DOCUMENTS

| CN | 102099942 A | 6/2011 |
|----|-------------|--------|
| JP | 05310949 A | 11/1993 |
| JP | 6200244 A | 7/1994 |
| JP | 8283416 A | 10/1996 |
| JP | 2002265614 | 9/2002 |
| JP | 2006278549 A | 10/2006 |
| JP | 2011525047 A | 9/2011 |

OTHER PUBLICATIONS

Kononenko et al. Journal of Molecular Liquids (2006), 127(1-3), 118-120.*
Bolink et al., "Efficient blue emitting organic light emitting diodes based on fluorescent solution processable cyclic phosphazenes" Organinc Electronics, V9 N2, p. 155-163 (Oct. 25, 2007).
Bolink et al., Solution Processable Phosphorescent Dendrimers based on Cyclic Phosphazenes for use in Organic Light Emitting Diodes (OLEDs)Chemical Communications, Dec. 4, 2007, p. 618-620.
Schrogel et al., "Phosphazene-Based Host Materials for the Use in Blue Phosphorescent Organic Light-Emitting Diodes" Chem. Mater., 23 (22), 4947-4953 (2011).
Kononenko et al., "Dynamics of electron-vibrational excitation of polyphosphazenes containing carbazole and coumarin" Journal of Molecular Liquids. 127:118-120 (2006).
International Search Report, dated May 27, 2014, in corresponding PCT International application No. PCT/JP2014/055427.
International Preliminary Report, dated Sep. 17, 2015, in corresponding PCT International application No. PCT/JP2014/055427.
Chinese Office Action dated Jul. 7, 2016 in corresponding Chinese Patent appl. No. 201480010314.8.

* cited by examiner

*Primary Examiner* — Kahsay Habte
(74) *Attorney, Agent, or Firm* — Browdy and Neimark, PLLC

(57) ABSTRACT

A compound represented by the following formula (1) is useful as a charge transporting material. $R^1$ to $R^6$ represent a group represented by the formula (2), $R^7$ represents an aryl group or an aralkyl group, and $R^{11}$ to $R^{15}$ represent a hydrogen atom or a substituent.

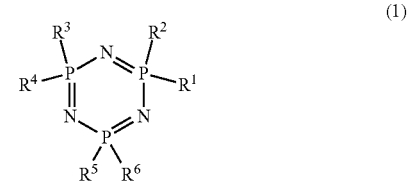

(1)

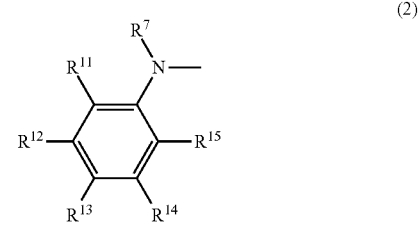

(2)

7 Claims, 5 Drawing Sheets

CHARGE TRANSPORT MATERIAL, HOST MATERIAL, THIN FILM AND ORGANIC LIGHT EMITTING ELEMENT

TECHNICAL FIELD

The present invention relates to a compound that is useful as a charge transporting material and a host material, and a thin film and an organic light emitting device that are produced by using the same.

BACKGROUND ART

An organic light emitting device, such as an organic electroluminescent device (organic EL device), has been actively studied for enhancing the light emission efficiency thereof. In particular, various studies for enhancing the light emitting efficiency have been made by newly developing and combining an electron transporting material, a hole transporting material, a light emitting material, a host material and the like constituting an organic electroluminescent device. Among these, there are studies relating to an organic light emitting device utilizing a compound containing a cyclotriphosphazene ring.

For example, Non-patent Document 1 describes that the compound represented by the following general formula is useful as a host material of a blue phosphorescent light emitting material. Non-patent Document 1 specifically describes a compound containing a cyclotriphosphazene ring having a 3,5-dimethylphenyl group bonded thereto, a compound containing a cyclotriphosphazene ring having a 4-methoxyphenyl group bonded thereto, and a compound containing a cyclotriphosphazene ring having an unsubstituted phenyl group bonded thereto. Non-patent Document 1 describes that the compounds have a decomposition temperature of from 280 to 330° C. and a T1 level (i.e., a lowest excitation triplet energy level) exceeding 3.0 eV.

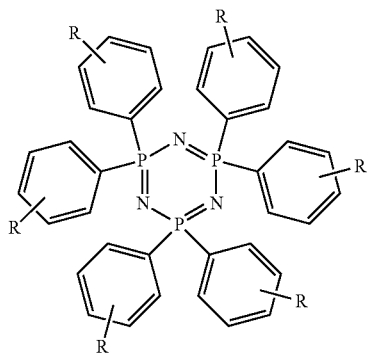

Patent Document 1 describes that the compound represented by the following general formula is useful as a host material of a phosphorescent light emitting material and a fluorescent light emitting material. In the following general formula, Y represents an aryl group, a heteroaryl group, a carbazolyl group or an azacarbazolyl group, which is bonded to the phosphorus atom of the cyclotriphosphazene ring through a carbon atoms. Patent Document 1 specifically describes the compounds, in which Y represents a 4-(carbazol-9-yl)phenyl group and an N-methylcarbazol-3-yl group, and the like. However, such a compound is not described that the group is bonded to the phosphorus atom of the cyclotriphosphazene ring through a nitrogen atom.

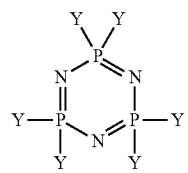

As for a compound having a group that is bonded to the phosphorus atom of the cyclotriphosphazene ring through a nitrogen atom, one compound is described in Non-patent Document 2. Non-patent Document 2 studies light emission characteristics of the compound represented by the aforementioned general formula, in which Y represents a carbazol-9-yl group. However, Non-patent Document 2 does not describe the usefulness of the compound as a charge transporting material and a host material.

CITATION LIST

Non-Patent Documents

Non-patent Document 1: Pamela Schrögel et al., Chem. Mater., 2011, 23 (22), 4947-4953

Non-patent Document 2: Yu. T. Kononenko et al., Journal of Molecular Liquids, 127 (2006), 118-120

Patent Document

Patent Document 1: JP-T-2011-525047

SUMMARY OF INVENTION

Technical Problem

As described above, the use of a compound having a cyclotriphosphazene ring in a light emitting device has been proposed. The compounds described in Non-patent Document 1 and Patent Document 1 have a high T1 level, but may not be said to have sufficiently high in thermal stability and light emission efficiency. Insufficient thermal stability may provide problems that the process for producing an organic light emitting device is restricted, and an intended device cannot be provided. Furthermore, in the case where the light emission efficiency cannot be sufficiently enhanced, the utility value of the compounds as a charge transporting material and a host material may be significantly impaired. In consideration of these problems in the related art, the present inventors have made earnest investigations for achieving, as an object, the improvement of the thermal stability and the light emission efficiency of the compound having a cyclotriphosphazene ring.

Solution to Problem

As a result of earnest investigations for achieving the object, the inventors have found that a compound having a particular structure has a high T1 level and excellent thermal stability, and also is useful as a charge transporting material. The inventors also have found that the compound is useful particularly as a host material of a blue light emitting material, and is capable of largely enhancing the light emission efficiency and the luminance of the organic light emitting device. Based on the knowledge, the inventors finally provide the following inventions as a measure for solving the problem.

(1) A charge transporting material containing a compound represented by the following general formula (1):

General Formula (1)

wherein in the general formula (1), $R^1$ to $R^6$ each independently represent a group represented by the following general formula (2):

General Formula (2)

wherein in the general formula (2), $R^7$ represents a substituted or unsubstituted aryl group or a substituted or unsubstituted aralkyl group; and $R^{11}$ to $R^{15}$ each independently represent a hydrogen atom or a substituent, and $R^7$ and $R^{11}$, $R^{11}$ and $R^{12}$, $R^{12}$ and $R^{13}$, $R^{13}$ and $R^{14}$, and $R^{14}$ and $R^{15}$ each may be bonded to each other to form a cyclic structure.

(2) The charge transporting material according to the item (1), wherein in the general formula (1), all $R^1$ to $R^6$ are the same as each other.

(3) The charge transporting material according to the item (1) or (2), wherein in the general formula (1), $R^1$ to $R^6$ each represent a group represented by one of the following general formulae (3) to (7):

General Formula (3)

General Formula (4)

General Formula (5)

General Formula (6)

General Formula (7)

wherein in the general formulae (3) to (7), $R^{21}$ to $R^{38}$, $R^{41}$ to $R^{48}$, $R^{51}$ to $R^{58}$, $R^{61}$ to $R^{65}$, and $R^{71}$ to $R^{79}$ each independently represent a hydrogen atom or a substituent, and $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{28}$ and $R^{29}$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, $R^{55}$ and $R^{65}$, $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, and $R^{78}$ and $R^{79}$ each may be bonded to each other to form a cyclic structure.

(4) The charge transporting material according to the item (3), wherein in the general formula (1), $R^1$ to $R^6$ each represent a group represented by the general formula (3).

(5) The charge transporting material according to the item (3) or (4), wherein in the general formula (1), $R^1$ to $R^6$ each represent a group represented by the following general formula (8):

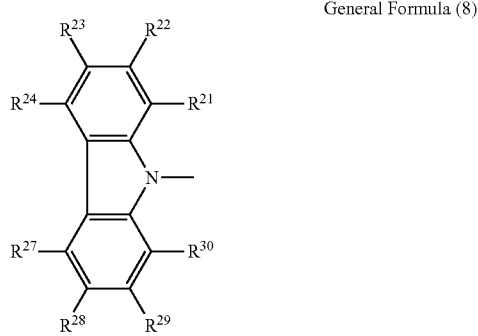

General Formula (8)

wherein in the general formula (8), $R^{21}$ to $R^{24}$, and $R^{27}$ to $R^{30}$ each independently represent a hydrogen atom or a substituent, and $R^{21}$ and $R^{22}$, $R^{22}$ and $R^{23}$, $R^{23}$ and $R^{24}$, $R^{27}$ and $R^{28}$, $R^{28}$ and $R^{29}$, and $R^{29}$ and $R^{30}$ each may be bonded to each other to form a cyclic structure.

(6) The charge transporting material according to the item (5), wherein the charge transporting material contains a compound having the following structure:

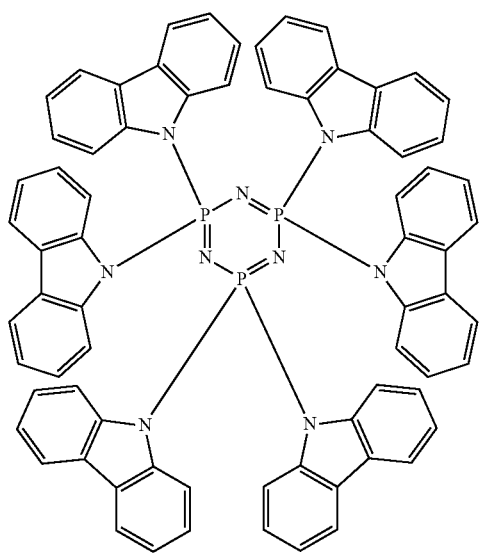 [SMILES: c1ccc2c(c1)c1ccccc1n2P1(n2c3ccccc3c3ccccc32)=NP(n2c3ccccc3c3ccccc32)(n2c3ccccc3c3ccccc32)=NP(n2c3ccccc3c3ccccc32)(n2c3ccccc3c3ccccc32)=N1]

wherein in the structure, any hydrogen atom may be substituted by a substituent.

(7) A host material containing the charge transporting material according to any one of the items (1) to (6).

(8) The host material according to the item (7), wherein the host material is for a blue light emitting material.

(9) A thin film containing the host material according to the item (7), and a light emitting material.

(10) The thin film according to the item (9), wherein the light emitting material is a blue light emitting material.

(11) An organic light emitting device containing the charge transporting material according to any one of the items (1) to (6).

(12) The organic light emitting device according to the item (11), wherein the charge transporting material is used in a light emitting layer as a host material.

(13) The organic light emitting device according to the item (11) or (12), wherein the organic light emitting material emits phosphorescent light.

(14) The organic light emitting device according to the item (11) or (12), wherein the organic light emitting material emits delayed fluorescent light.

(15) The organic light emitting device according to any one of the items (11) to (14), wherein the organic light emitting device is an organic electroluminescent device.

Advantageous Effects of Invention

The compound represented by the general formula (1) is useful as a charge transporting material. The compound is also useful as a host material in the case where a light emitting material is used as a dopant. The use of the host material of the invention may provide an organic light emitting device that has a high light emission efficiency and a large maximum luminance.

DESCRIPTION OF EMBODIMENTS

Figure 1:
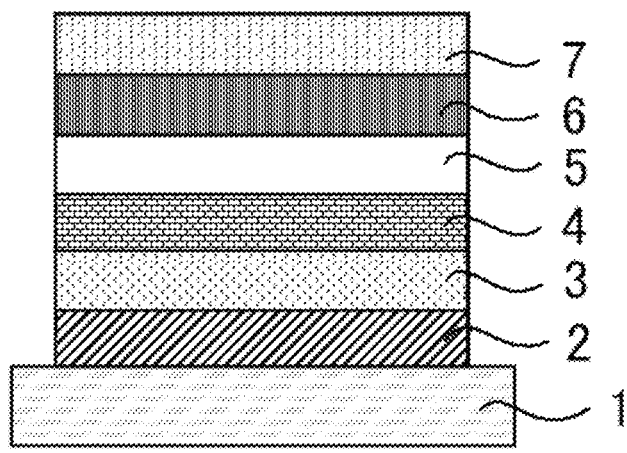
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the compound used in the invention is not particularly limited in isotope species, and for example, all the hydrogen atoms in the molecule may be $^1$H, and all or a part of them may be $^2$H (deuterium (D)).

Compound Represented by General Formula (1)

The charge transporting material of the invention contains a compound represented by the following general formula (1).

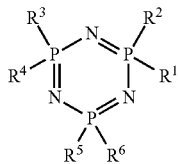

General Formula (1)

In the general formula (1), $R^1$ to $R^6$ each independently represent a group represented by the following general formula (2).

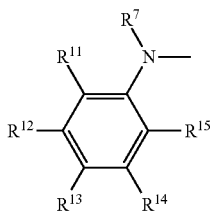

General Formula (2)

In the general formula (2), $R^7$ represents a substituted or unsubstituted aryl group or a substituted or unsubstituted aralkyl group.

The aromatic ring constituting the aryl group referred herein may be a monocyclic ring or a condensed ring, and specific examples thereof include a benzene ring, a naphthalene ring, an anthracene ring and a phenanthrene ring. The aryl group preferably has from 6 to 40 carbon atoms, more preferably from 6 to 20 carbon atoms, and further preferably from 6 to 14 carbon atoms. Specific examples of the aryl group include a phenyl group, a 1-naphthyl group, a 2-naphthyl group, a 1-anthracenyl group, a 2-anthracenyl group and a 9-anthracenyl group.

The aralkyl group referred herein means an alkyl group having at least one aryl group substituted thereon, and the alkyl moiety may be linear or branched. The alkyl moiety preferably has from 1 to 20 carbon atoms, more preferably from 1 to 10 carbon atoms, and further preferably from 1 to 5 carbon atoms. The aromatic ring constituting the aryl moiety may be a monocyclic ring or a condensed ring. For the specific examples and the preferred number of carbon atoms thereof, reference may be made to the aforementioned specific examples and the preferred ranges for the aryl group. The aryl group constituting the aralkyl group preferably bonded to the 1-position of the alkyl group. In the case where the aralkyl group has two or more constitutional aryl groups, the aryl groups may be the same as or different from each other. Specific examples of the aralkyl group include a phenylmethyl group, a 1-phenylethyl group, a 1-phenylpropyl group, a 1-phenylbutyl group, a 1-phenylpentyl group, a 1-phenylhexyl group, a naphthalen-1-ylmethyl group, a 1-(naphthalen-1-yl)ethyl group, a napthalen-2-ylmethyl group and a 1-(naphthalen-2-yl)ethyl group.

In the general formula (2), $R^7$ and $R^{11}$ may be bonded to each other to form a cyclic structure. The cyclic structure formed is preferably a 5-membered to 7-membered ring, and more preferably a 5-membered or 6-membered ring. The atoms constituting the ring skeleton thus formed may or may not contain a hetero atom other than the nitrogen atom bonded to $R^7$ and $R^{11}$. In the case where a hetero atom is contained, examples of the hetero atom contained include a nitrogen atom, a sulfur atom and an oxygen atom. Preferred examples of the cyclic structure include a 1,4-oxazine ring, a 1,4-thiazine ring, a pyrazine ring and a pyrrole ring. In the case where a pyrazine ring is formed, to the nitrogen atom at the 4-position thereof, a substituted or unsubstituted alkyl group or a substituted or unsubstituted aryl group is preferably bonded, a substituted or unsubstituted aryl group is more preferably bonded, and a substituted or unsubstituted phenyl group is further preferably bonded.

In the general formula (2), $R^{11}$ to $R^{15}$ each independently represent a hydrogen atom or a substituent. The number of the substituent is not particularly limited, and all $R^{11}$ to $R^{15}$ may be unsubstituted (i.e., hydrogen atoms). In the case where two or more of $R^{11}$ to $R^{15}$ each are a substituent, the plural substituents may be the same as or different from each other. Examples of the substituent capable of being represented by $R^{11}$ to $R^{15}$ and examples of the substituent capable of being represented by $R^7$, which represents the aryl group or the aralkyl group, include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituents include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms and a dialkyl-substituted amino group having from 1 to 10 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms and a substituted or unsubstituted heteroaryl group having from 3 to 12 carbon atoms.

In the general formula (2), $R^{11}$ and $R^{12}$, $R^{12}$ and $R^{13}$, $R^{13}$ and $R^{14}$, and $R^{14}$ and $R^{15}$ each may be bonded to each other to form a cyclic structure. The cyclic structure may be an aromatic ring or an aliphatic ring, and may contain a hetero atom, and the cyclic structure may be a condensed ring containing two or more rings. The hetero atom herein is preferably one selected from the group consisting of a nitrogen atom, an oxygen atom and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring and a cycloheptene ring.

In the general formula (1), all $R^1$ to $R^6$ may be the same as each other or different from each other. A part of them may be the same as each other. Examples of the case include the case where $R^1$ and $R^2$ are the same as each other, $R^3$ and $R^4$ are the same as each other, and $R^5$ and $R^6$ are the same as each other, and the case where $R^1$, $R^3$ and $R^5$ are the same as each other, and $R^2$, $R^4$ and $R^6$ are the same as each other. The compound having $R^1$ to $R^6$ that are all the same as each other has an advantage that the compound may be easily synthesized.

In the general formula (1), $R^1$ to $R^6$ each preferably represent a group represented by one of the following general formulae (3) to (7):

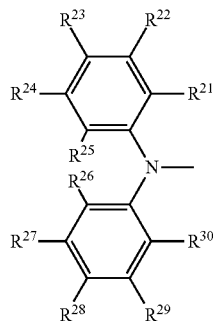

General Formula (3)

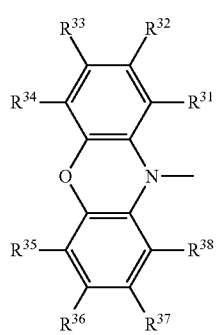

General Formula (4)

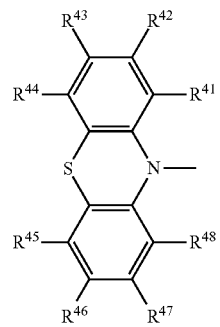

General Formula (5)

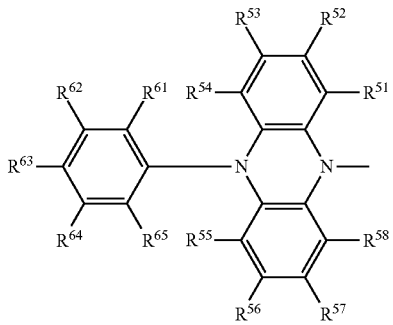

General Formula (6)

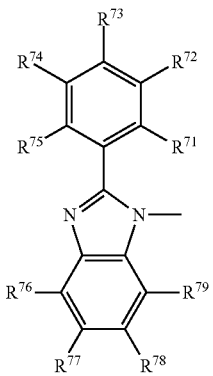

General Formula (7)

In the general formulae (3) to (7), $R^{21}$ to $R^{38}$, $R^{41}$ to $R^{48}$, $R^{51}$ to $R^{58}$, $R^{61}$ to $R^{65}$, and $R^{71}$ to $R^{79}$ each independently represent a hydrogen atom or a substituent. For the description and the preferred ranges of the substituent herein, reference may be made to the description and the preferred ranges for the substituent capable of being represented by $R^{11}$ to $R^{15}$. In the general formulae (3) to (7), the number of the substituent is not particularly limited. The case where all of them are unsubstituted (i.e., hydrogen atoms) is also preferred. In the case where two or more substituents are present in each of the general formula (3) to (7), the plural substituents may be the same as or different from each other. In the case where a substituent is present in the general formulae (3) to (7), the substituent is preferably any of $R^{22}$ to $R^{24}$ and $R^{27}$ to $R^{29}$ for the general formula (3), any of $R^{32}$ to $R^{37}$ for the general formula (4), any of $R^{42}$ to $R^{47}$ for the general formula (5), any of $R^{52}$, $R^{53}$, $R^{56}$, $R^{57}$ and $R^{62}$ to $R^{64}$ for the general formula (6), and any of $R^{72}$ to $R^{74}$, $R^{77}$ and $R^{78}$ for the general formula (7).

In the general formulae (3) to (7), $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{28}$ and $R^{29}$, $R^{29}$ and $R^{30}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{64}$ and $R^{65}$, $R^{54}$ and $R^{61}$, $R^{55}$ and $R^{65}$, $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, and $R^{78}$ and $R^{79}$ each may be bonded to each other to form a cyclic structure. For the description and the preferred examples of the cyclic structure, reference may be made to the description and the preferred examples for the cyclic structure formed by bonding $R^{11}$ and $R^{12}$, and the like in the general formula (2).

In the general formula (1), all $R^1$ to $R^6$ preferably represent a group represented by one of the general formulae (3) to (7). Preferred examples of the case include the case where all $R^1$ to $R^6$ preferably represent a group represented by the general formula (3). In this case, $R^1$ to $R^6$ may be the same groups or different groups.

In the general formula (1), $R^1$ to $R^6$ each preferably represent a group represented by the following general formula (8). The general formula (8) has a structure in which $R^{25}$ and $R^{26}$ in the general formula (3) are bonded to each other through a single bond:

General Formula (8)

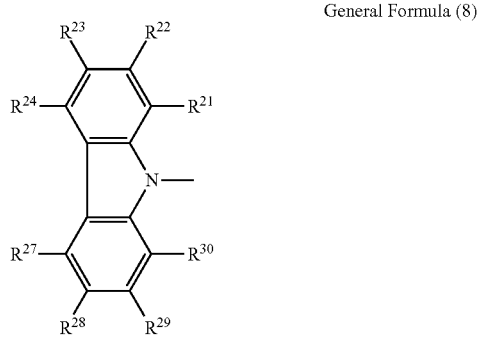

In the general formula (8), $R^{21}$ to $R^{24}$, and $R^{27}$ to $R^{30}$ each independently represent a hydrogen atom or a substituent. $R^{21}$ and $R^{22}$, $R^{22}$ and $R^{23}$, $R^{23}$ and $R^{24}$, $R^{27}$ and $R^{28}$, $R^{28}$ and $R^{29}$, and $R^{29}$ and $R^{30}$ each may be bonded to each other to form a cyclic structure. For the description of the substituent and the description for the cyclic structure, reference may be made to the corresponding descriptions for the general formulae (2) and (3).

Preferred examples of the compound represented by the general formula (1) include a compound having the following structure. In the structure, any hydrogen atom may be substituted by a substituent. For the description and the preferred ranges of the substituent, reference may be made to the corresponding descriptions for the general formulae (2) and (3).

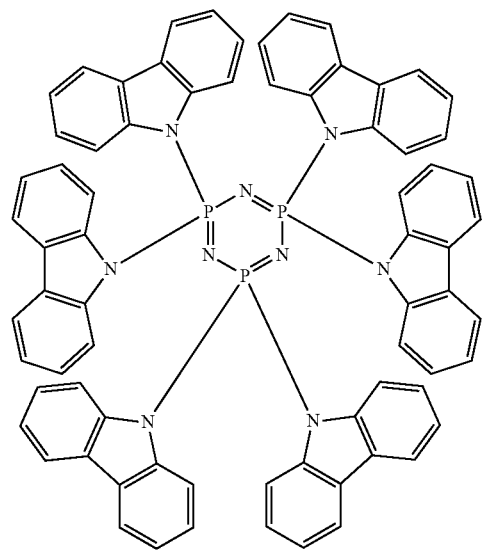

Specific examples of the compound represented by the general formula (1) are shown below. However, the compound represented by the general formula (1) capable of being used in the invention is not construed as being limited to the specific examples.

Compound 1

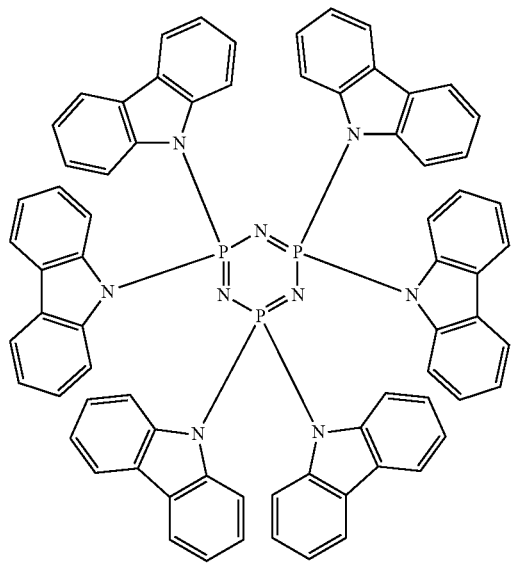

-continued
Compound 2
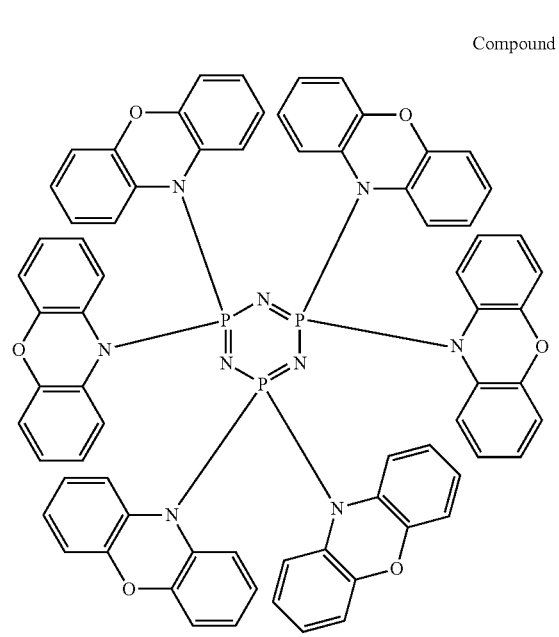
Compound 4
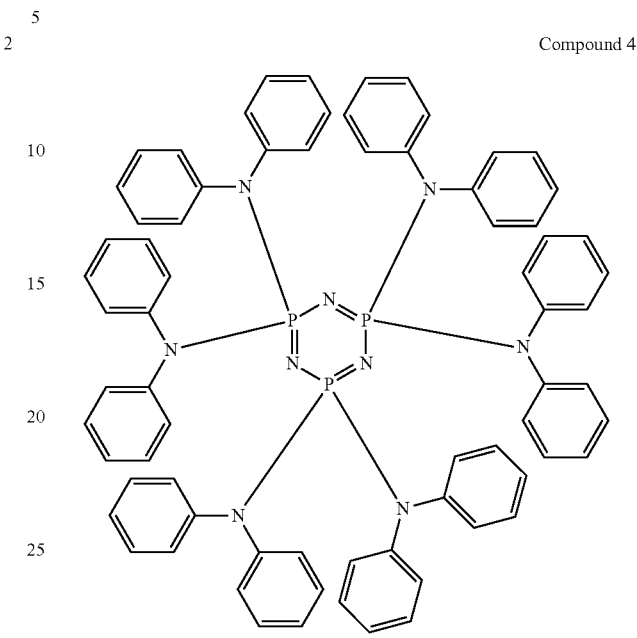
Compound 3
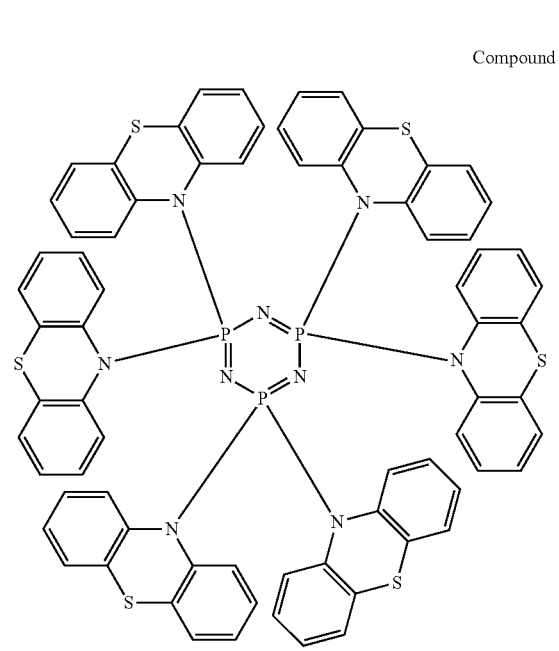
Compound 5
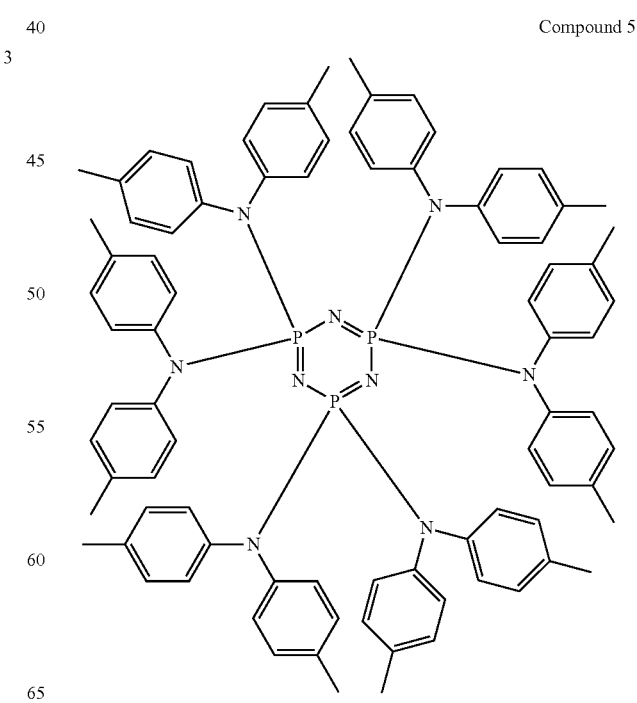

-continued

Compound 6

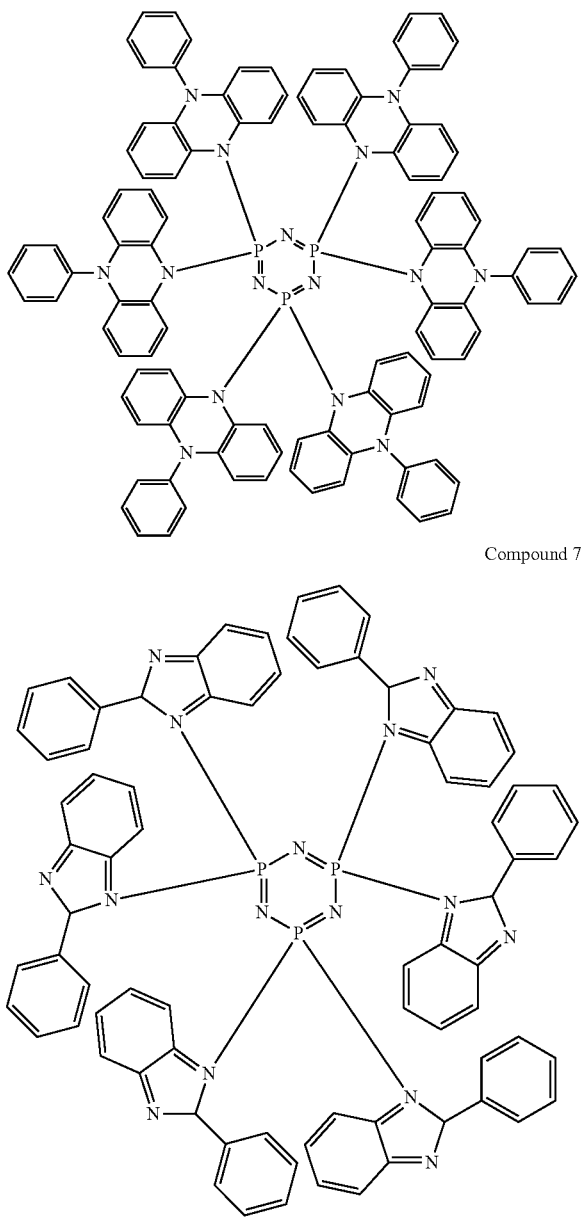

Compound 7

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method and used. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a light emitting material.

For example, it may be considered that a polymerizable group is introduced in advance to the structure represented by the general formula (1), and a polymer obtained by polymerizing the polymerizable group is used as a light emitting material. Specifically, it may be considered that a monomer that has a polymerizable functional group at any of $R^1$ to $R^6$ in the general formula (1) is prepared, and is homopolymerized or copolymerized with another monomer to prepare a polymer containing repeating units, and the polymer is used as a light emitting material. In alternative, it may be considered that the compounds represented by the general formula (1) are coupled to form a dimer or a trimer, and the dimer or the trimer is used as a light emitting material.

Examples of the polymer having the repeating unit containing the structure represented by the general formula (1) include a polymer containing a structure represented by the following general formula (9) or (10).

General Formula (9)

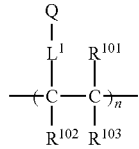

General Formula (10)

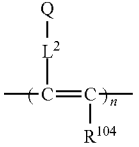

In the general formulae (9) and (10), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $-X^{11}-L^{11}-$, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (9) and (10), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably a substituted or unsubstituted alkyl group having from 1 to 3 carbon atoms, a substituted or unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $R^1$ to $R^6$ in the structure of the general formula (1) constituting Q, any of $R^7$ and $R^{11}$ to $R^{15}$ in the structure of the general formula (2), any of $R^{21}$ to $R^{30}$ in the structure of the general formula (3), any of $R^{31}$ to $R^{38}$ in the structure of the general formula (4), any of $R^{41}$ to $R^{48}$ in the structure of the general formula (5), any of $R^{51}$ to $R^{58}$ and $R^{61}$ to $R^{65}$ in the structure of the general formula (6), or any of $R^{71}$ to $R^{78}$ in the structure of the general formula (7). Two or more of the linking groups may be boded to one group represented by Q to form a crosslinked structure or a network structure.

Specific examples of the structure of the repeating unit include structures represented by the following formulae (11) to (14).

Formula (11)
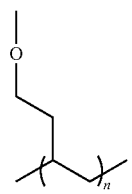

Formula (12)
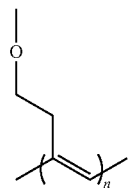

Formula (13)
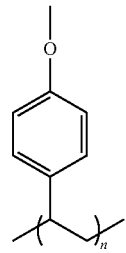

Formula (14)
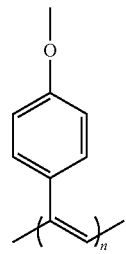

The polymer having the repeating unit containing the structure represented by any of the formulae (11) to (14) may be synthesized in such a manner that a hydroxyl group is introduced to any of $R^1$ to $R^6$ in the structure represented by the general formula (1), and the hydroxyl group as a linker is reacted with the following compound to introduce a polymerizable group thereto, followed by polymerizing the polymerizable group.

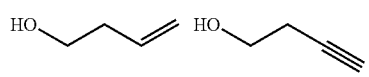

-continued
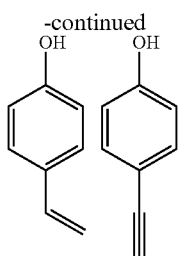

The polymer containing the structure represented by the general formula (1) may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Synthesis Method of Compound Represented by General Formula (1)

The compound represented by the general formula (1) may be synthesized by combining the known synthesis methods. For example, the compound may be synthesized through the following reaction scheme.

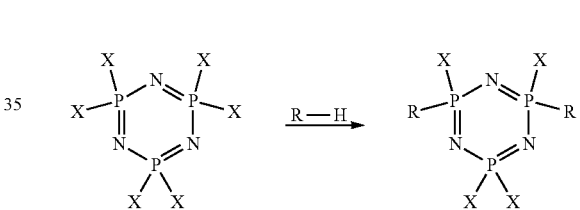

In the aforementioned reaction scheme, R has the same definition as $R^1$ to $R^6$ in the general formula (1). The reaction scheme shows the synthesis method of the compound having $R^1$ to $R^6$ that are all the same as each other. In the reaction scheme, X represents a halogen atom, examples of which include a fluorine atom, a chlorine atom, a bromine atom and an iodine atom, with a chlorine atom and a bromine atom being preferred.

The reaction shown by the reaction scheme is an application of the known coupling reaction, and the known reaction conditions may be appropriately selected and used. For example, the compound may be synthesized by using NaH in DMF. The compound represented by the general formula (1) may also be synthesized by combining the other known synthesis reactions.

Application of Compound Represented by General Formula (1)

The compound represented by the general formula (1) is useful as a charge transporting material. In particular, the compound is useful as a host material that assumes the combination use with a light emitting material as a dopant. A thin film containing the compound represented by the general formula (1) along with a light emitting material may achieve a high light emission efficiency and a high luminance. The compound represented by the general formula (1) is preferably used in combination with a blue light emitting material, in particular, since a high blue light emission efficiency and a high luminance may be achieved. For achieving a high blue light emission efficiency and a high luminance by the combination use with a blue light emitting material, it is said that the compound necessarily has a high T1 level and a large band gap. In general, a material that has a high T1 level has a problem of deteriorated thermal stability. The cyclotriphosphazene compound described in Non-patent Document 1 (Chem. Mater., 2011, 23 (22), 4947-4953) has a high T1 level, but may not be said to have sufficiently high in thermal stability. Although a solution to the problem has not yet been provided, the compound represented by the general formula (1) proposed in the invention has excellent characteristics, i.e., the compound not only has a high T1 level but also has high thermal stability. The thermal decomposition temperature of the compound represented by the general formula (1) is preferably 330° C. or more, more preferably 350° C. or more, and further preferably 380° C. or more. The thermal decomposition temperature referred herein means such a temperature, at which the compound exhibits a weight loss of 5% by weight or more on heating the compound.

The compound represented by the general formula (1) has high thermal stability and thus has such advantages as high applicability to formation of a thin film and a production process of an organic light emitting device. The compound represented by the general formula (1) is easily sublimated due to the relatively low molecular weight thereof, and thus has high applicability to production of devices. For example, the hexaphenylcyclotriphosphazene substituted with six carbazol-9-yl groups described in Patent Document 1 (JP-A-2011-525047) is limited in application ranges in the practical industrial fields due to the inferior sublimation property thereof, and thus is low in industrial applicability.

The compound represented by the general formula (1) not only has the aforementioned characteristics, but also has such characteristics that a thin film thereof formed with a light emitting material may achieve a highlight emission efficiency and a high luminance. The compound represented by the general formula (1) has a sufficiently deep HOMO energy level. For example, as compared to the hexaphenyl-cyclotriphosphazene substituted with six carbazol-9-yl groups, the HOMO energy level of the compound represented by the general formula (1) is apparently deep. Accordingly, the compound represented by the general formula (1) has a relatively large band gap and thus is significantly effective as a host material for a blue light emitting material. The band gap of the compound represented by the general formula (1) is preferably 3.0 eV or more, more preferably 3.5 eV or more, and further preferably 3.8 eV or more.

A light emitting material that may be used in combination with the compound represented by the general formula (1) may be any of a phosphorescent light emitting material, a fluorescent light emitting material, and a material that emits delayed fluorescent light. Among these, the combination with alight emitting material that emits delayed fluorescent light (i.e., a delayed fluorescent material) may drastically enhance the light emission efficiency and the luminance. The principle of the features may be described as follows for an organic electroluminescent device as an example.

In an organic electroluminescent device, carriers are injected from an anode and a cathode to a light emitting material to form an excited state for the light emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy use efficiency. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited single state has the same wavelength as fluorescent light since it is light emission from the excited single state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited single state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The light emitting material that may be used in combination with the compound represented by the general formula (1) is preferably a blue light emitting material, but light emitting materials that emit light of other colors may also be used in combination. The blue light emitting material used herein may be compounds having been known in the art. Examples thereof include coumarin, perylene, pyrene, anthracene, p-bis(2-phenylethenyl)benzene, and derivatives of these compounds. Preferred examples of the light emitting material that may be used in combination with the compound represented by the general formula (1) include the following compounds.

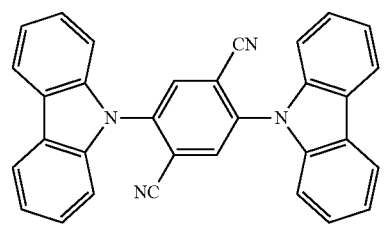

-continued

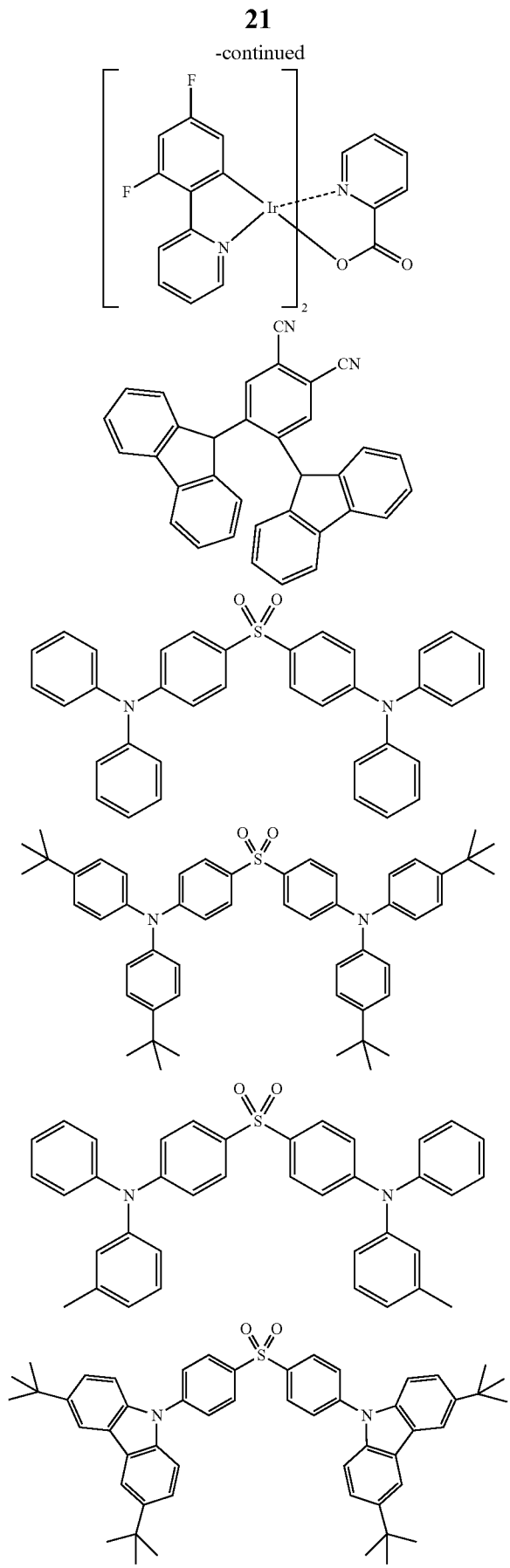

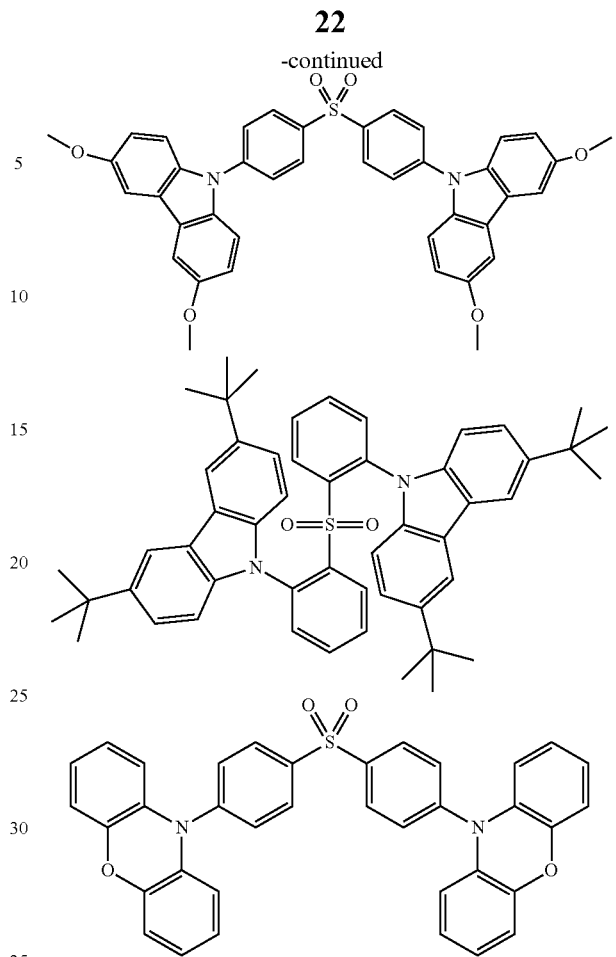

The use of the compound represented by the general formula (1) of the invention as a charge transporting material or a host material for a light emitting layer may provide an excellent organic light emitting device, such as an organic photoluminescent device (organic PL device) and an organic electroluminescent device (organic EL device). At this time, the compound represented by the general formula (1) of the invention may have a function of assisting light emission of another light emitting material contained in the light emitting layer, i.e., as a so-called assist dopant. Specifically, the compound represented by the general formula (1) of the invention contained in the light emitting layer may have a lowest excited singlet energy that is between the lowest excited singlet energy of the host material contained in the light emitting layer and the lowest excited singlet energy of the another light emitting material contained in the light emitting layer.

The organic photoluminescent device has a structure containing a substrate having formed thereon at least a light emitting layer. The organic electroluminescent device has a structure containing at least an anode, a cathode and an organic layer formed between the anode and the cathode. The organic layer contains at least a light emitting layer, and may be formed only of a light emitting layer, or may have one or more organic layer in addition to the light emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light emitting layer, 6 denotes an electron transporting layer, and 7 denotes a cathode.

The members and the layers of the organic electroluminescent device will be described below. The descriptions for the substrate and the light emitting layer may also be applied to the substrate and the light emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 µm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 µm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light Emitting Layer

The light emitting layer is a layer, in which holes and electrons injected from the anode and the cathode, respectively, are recombined to form excitons, and then the layer emits light. A light emitting material may be solely used as the light emitting layer, but the light emitting layer preferably contains a light emitting material and a host material. The host material used may be one kind or two or more kinds selected from the group of compounds represented by the general formula (1). In order that the organic electroluminescent device and the organic photoluminescent device of the invention exhibit a high light emission efficiency, it is important that the singlet excitons and the triplet excitons generated in the light emitting material are confined in the light emitting material. Accordingly, the host material represented by the general formula (1) is preferably used in addition to a light emitting material in the light emitting layer. The host material used may be an organic compound that has excited singlet energy and excited triplet energy, at least one of which is higher than those of the light emitting material. As a result, the singlet excitons and the triplet excitons generated in the light emitting material are capable of being confined in the molecules of the light emitting material, thereby eliciting the light emission efficiency thereof sufficiently. Even though the singlet excitons and the triplet excitons are not confined sufficiently, a high light emission efficiency may be obtained in some cases, and thus the host material that is capable of achieving a high light emission efficiency may be used in the invention without any particular limitation. In the organic light emitting device and the organic electroluminescent device of the invention, the light emission occurs in the light emitting material contained in the light emitting layer. The emitted light may be any of phosphorescent light, fluorescent light and delayed fluorescent light, and may contain plural kinds thereof. However, a part of the emitted light may contain emitted light from the host material, or the emitted light may partially contain emitted light from the host material.

In the case where the host material is used, the amount of the compound which is the light emitting material contained in the light emitting layer is preferably 0.1% by weight or more, and more preferably 1% by weight or more, and is preferably 50% by weight or less, more preferably 20% by weight or less, and further preferably 10% by weight or less.

The host material in the light emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light emitting layer or the hole transporting layer and between the cathode and the light emitting layer or the electron transporting layer. The injection layer may be provided depending on necessity.

Barrier Layer

The barrier layer is a layer that is capable of inhibiting charges (electrons or holes) and/or excitons present in the light emitting layer from being diffused outside the light emitting layer. The electron barrier layer may be disposed between the light emitting layer and the hole transporting layer, and inhibits electrons from passing through the light emitting layer toward the hole transporting layer. Similarly, the hole barrier layer may be disposed between the light emitting layer and the electron transporting layer, and inhibits holes from passing through the light emitting layer toward the electron transporting layer. The barrier layer may also be used for inhibiting excitons from being diffused outside the light emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light emitting layer.

Exciton Barrier Layer

The exciton barrier layer is a layer for inhibiting excitons generated through recombination of holes and electrons in the light emitting layer from being diffused to the charge transporting layer, and the use of the layer inserted enables effective confinement of excitons in the light emitting layer, and thereby enhances the light emission efficiency of the device. The exciton barrier layer may be inserted adjacent to the light emitting layer on any of the side of the anode and the side of the cathode, and on both the sides. Specifically, in the case where the exciton barrier layer is present on the side of the anode, the layer may be inserted between the hole transporting layer and the light emitting layer and adjacent to the light emitting layer, and in the case where the layer is inserted on the side of the cathode, the layer may be inserted between the light emitting layer and the cathode and adjacent to the light emitting layer. Between the anode and the exciton barrier layer that is adjacent to the light emitting layer on the side of the anode, a hole injection layer, an electron barrier layer and the like may be provided, and between the cathode and the exciton barrier layer that is adjacent to the light emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used as a host material of the light emitting layer, and may be used as a charge transporting layer in the other layers. In this case, the compound represented by the general formula (1) used in the light emitting layer and the compound represented by the general formula (1) used in the other layers than the light emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_2$ to $R_7$ each independently represent a hydrogen atom or a substituent, and n represents an integer of from 3 to 5.

Specific examples of a compound that may be used as the host material of the light emitting layer in the case where the compound represented by the general formula (1) is used in the other layers than the light emitting layer are shown below.

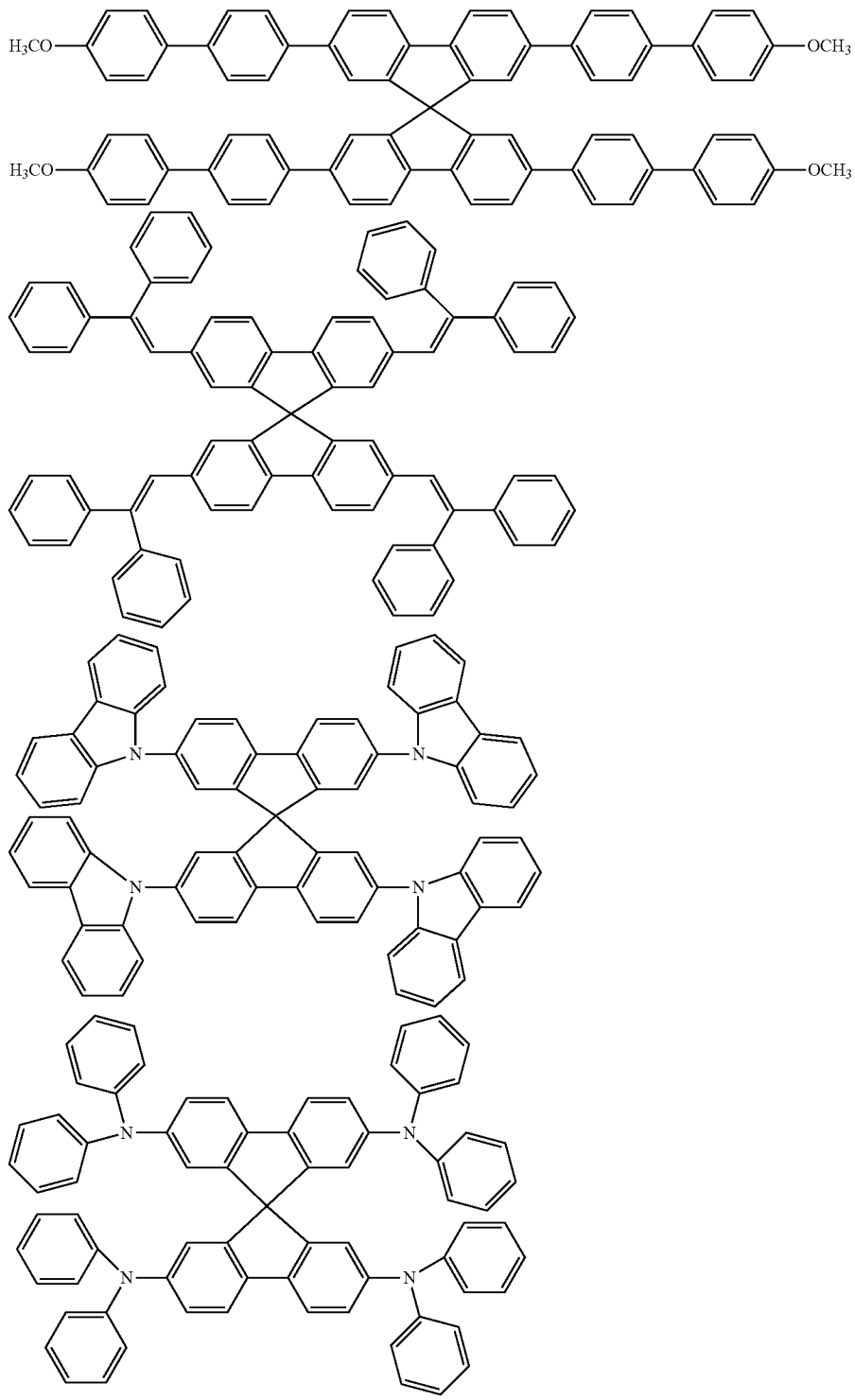

-continued
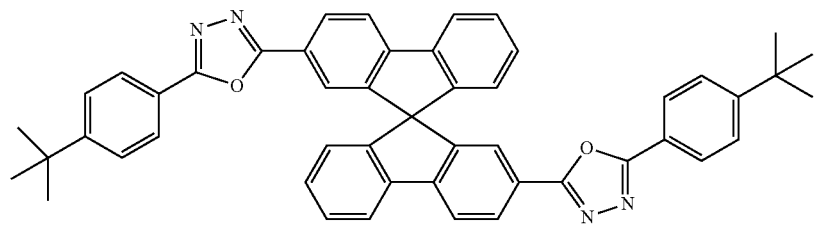
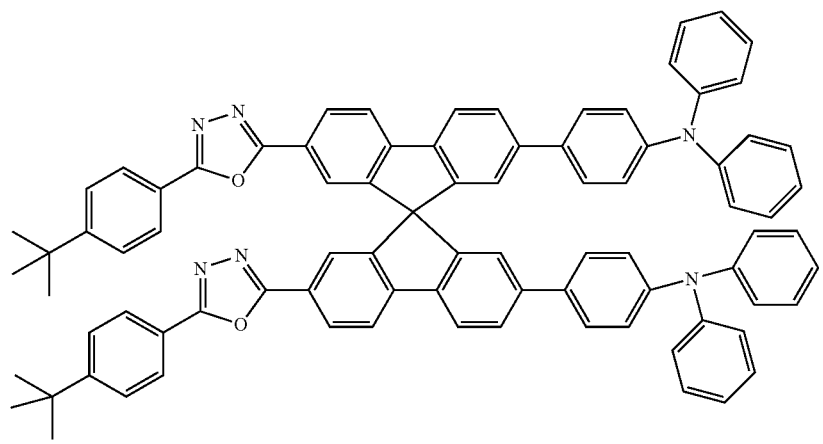
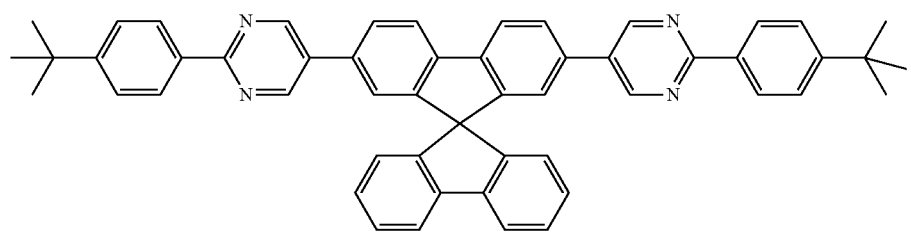
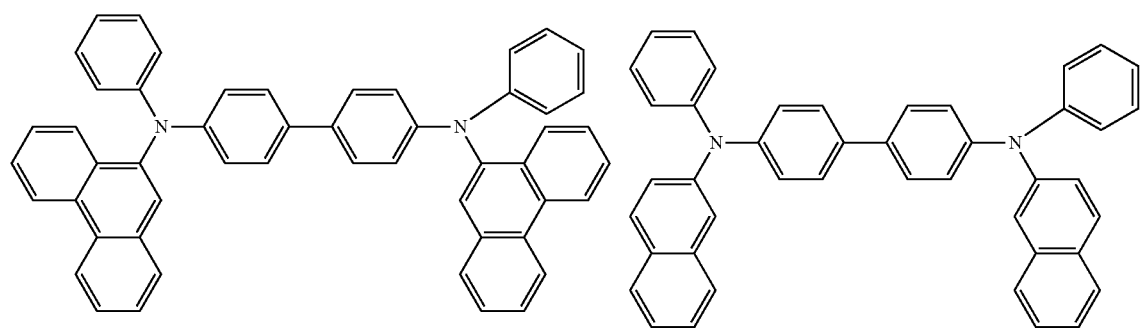
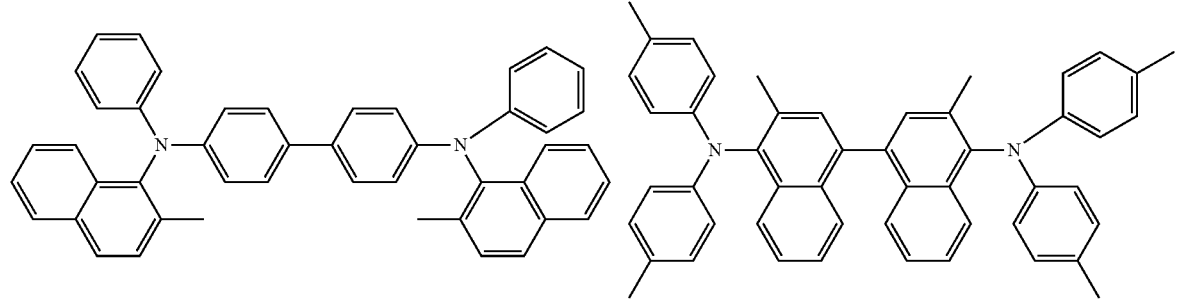

-continued
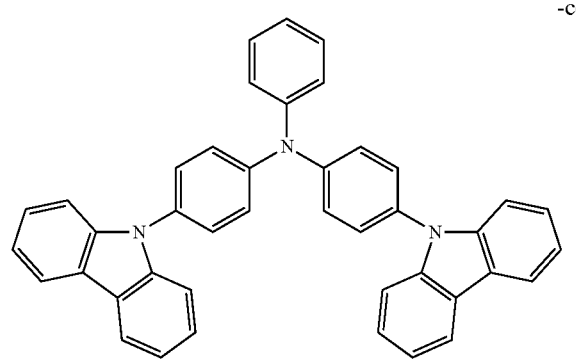
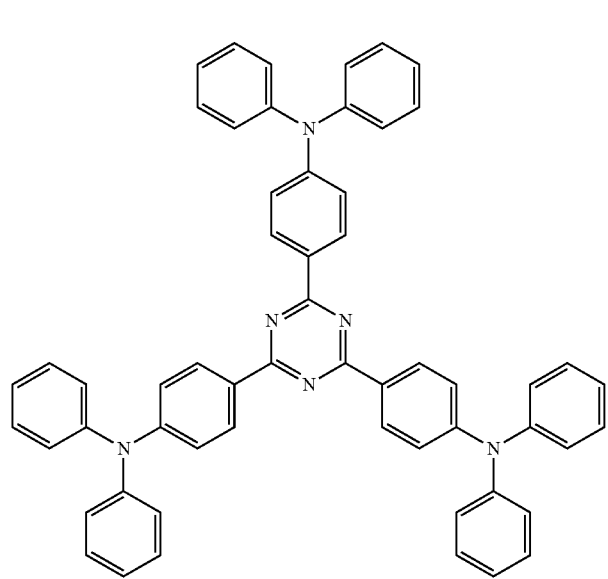
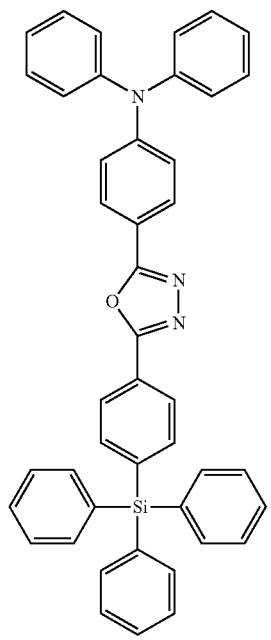
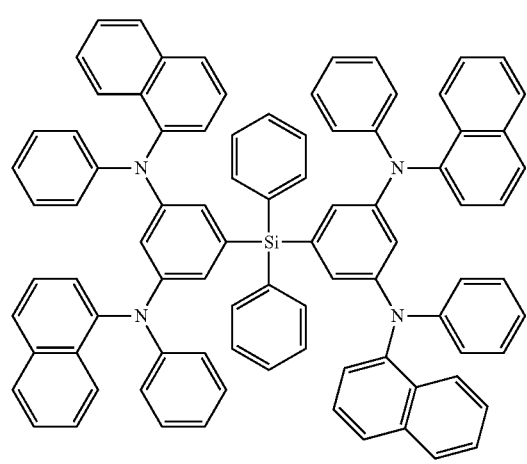
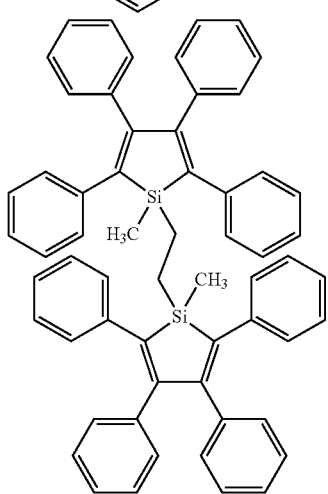
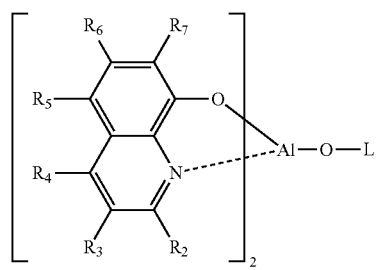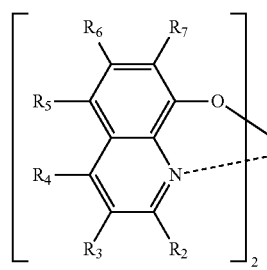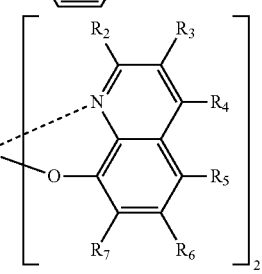

-continued
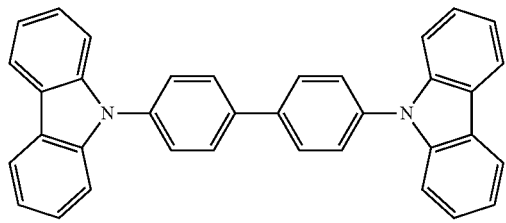
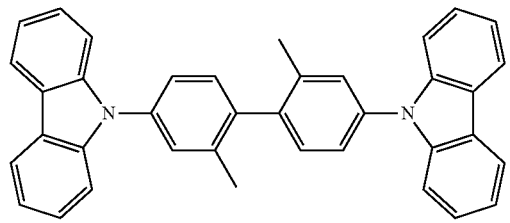
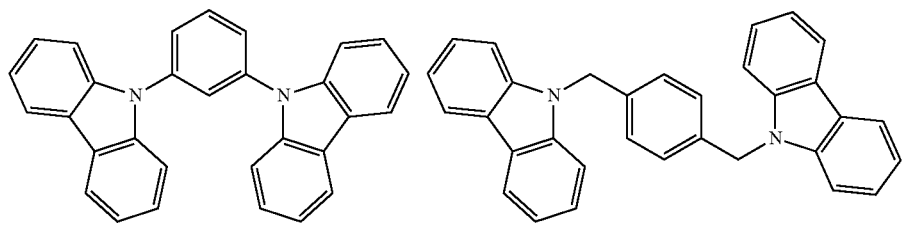
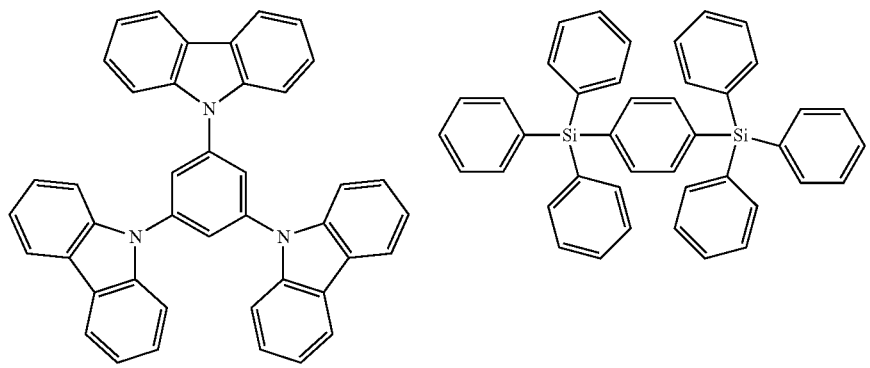
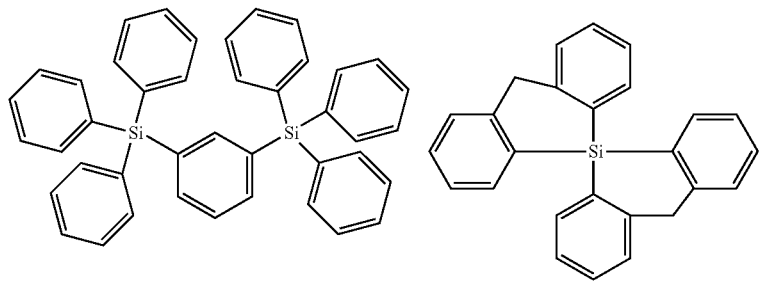
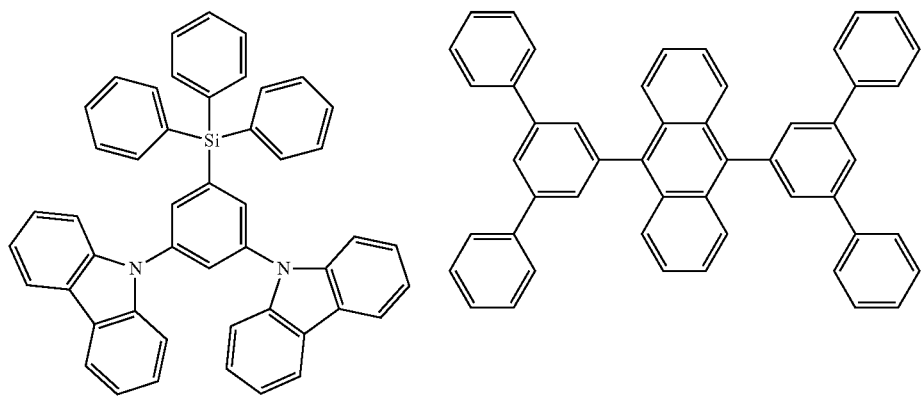

-continued
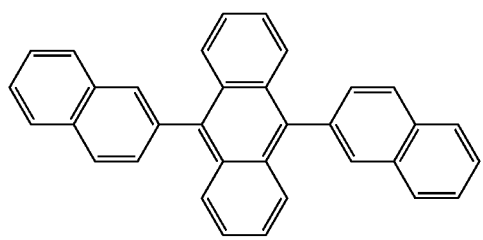
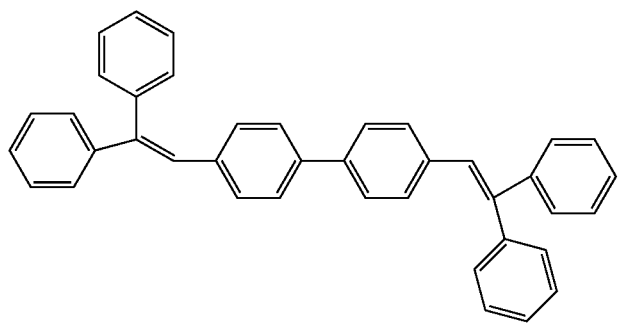
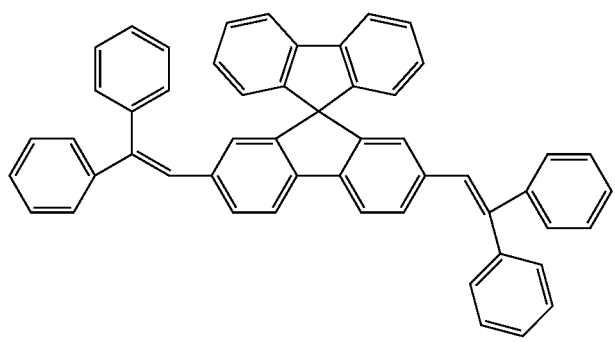
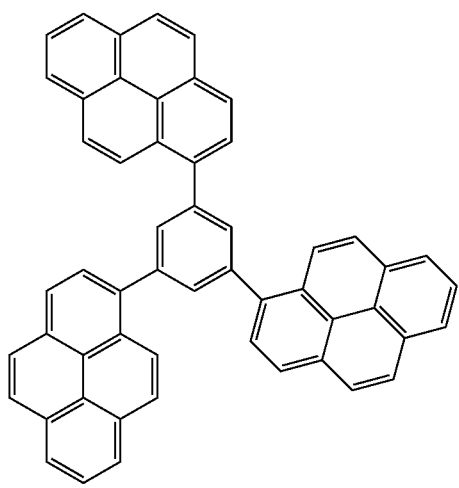

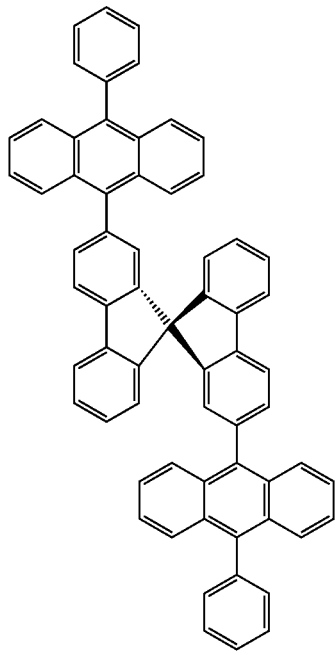
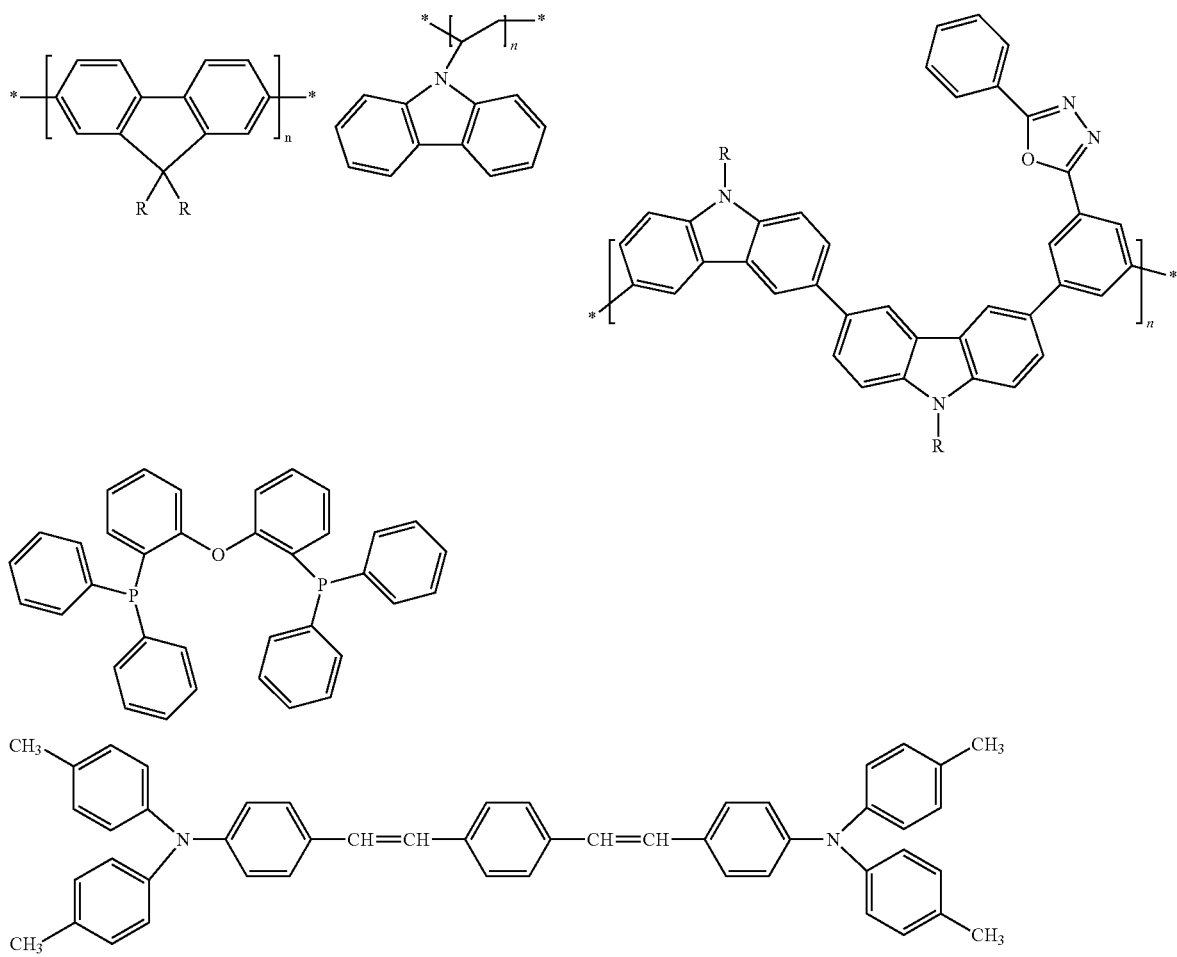

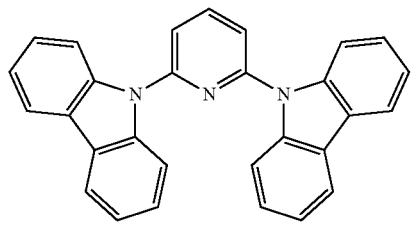
Preferred examples of a compound that may be used as the hole injection material are shown below.
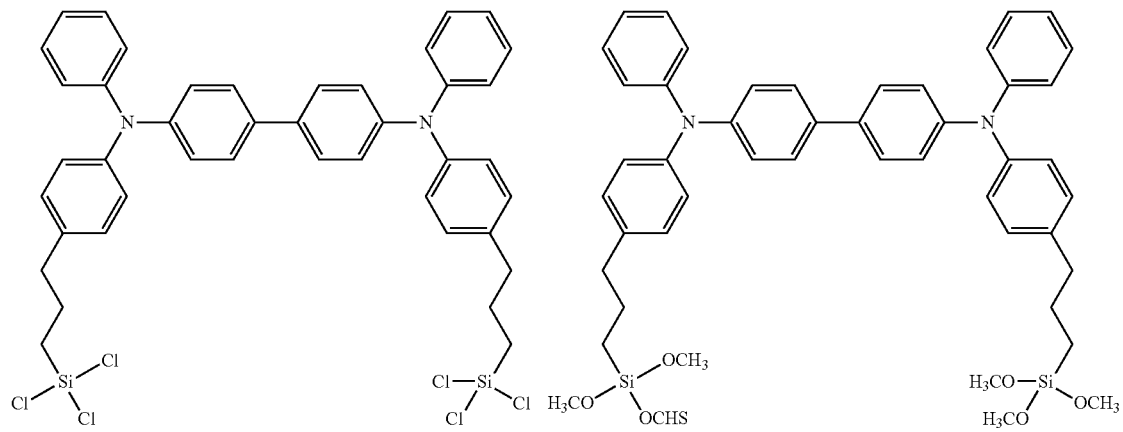
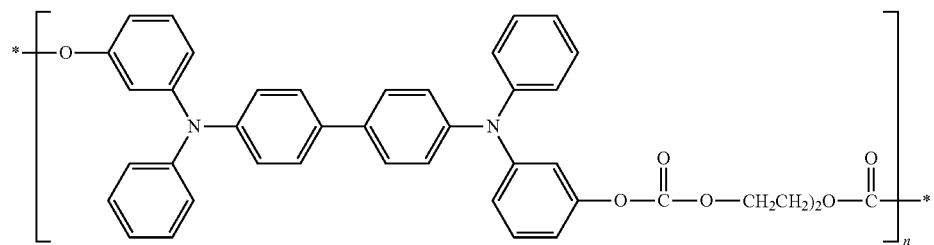
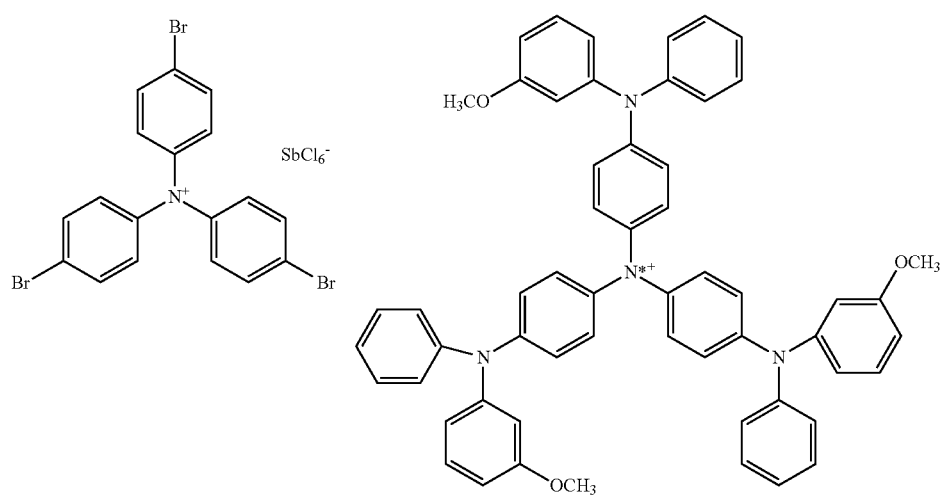

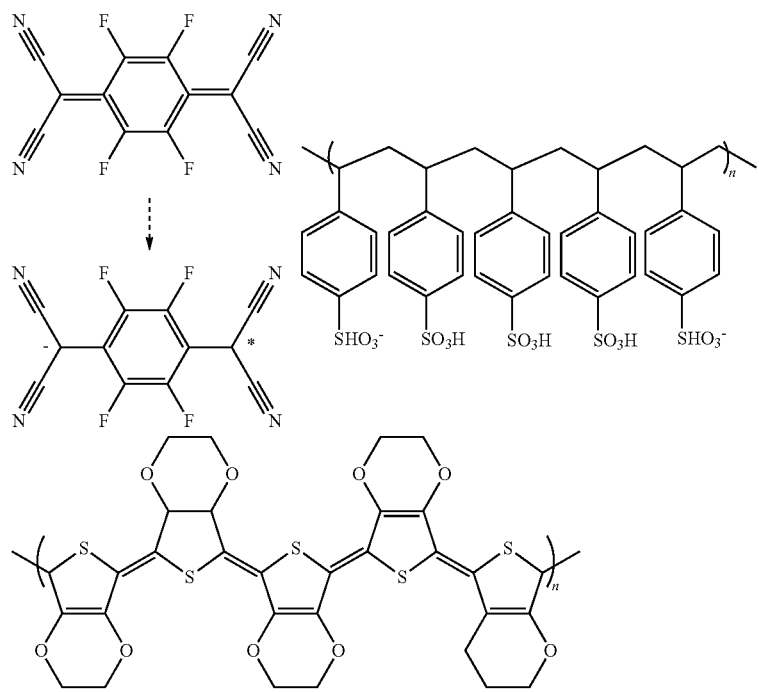
Preferred examples of a compound that may be used as the hole transporting material are shown below.
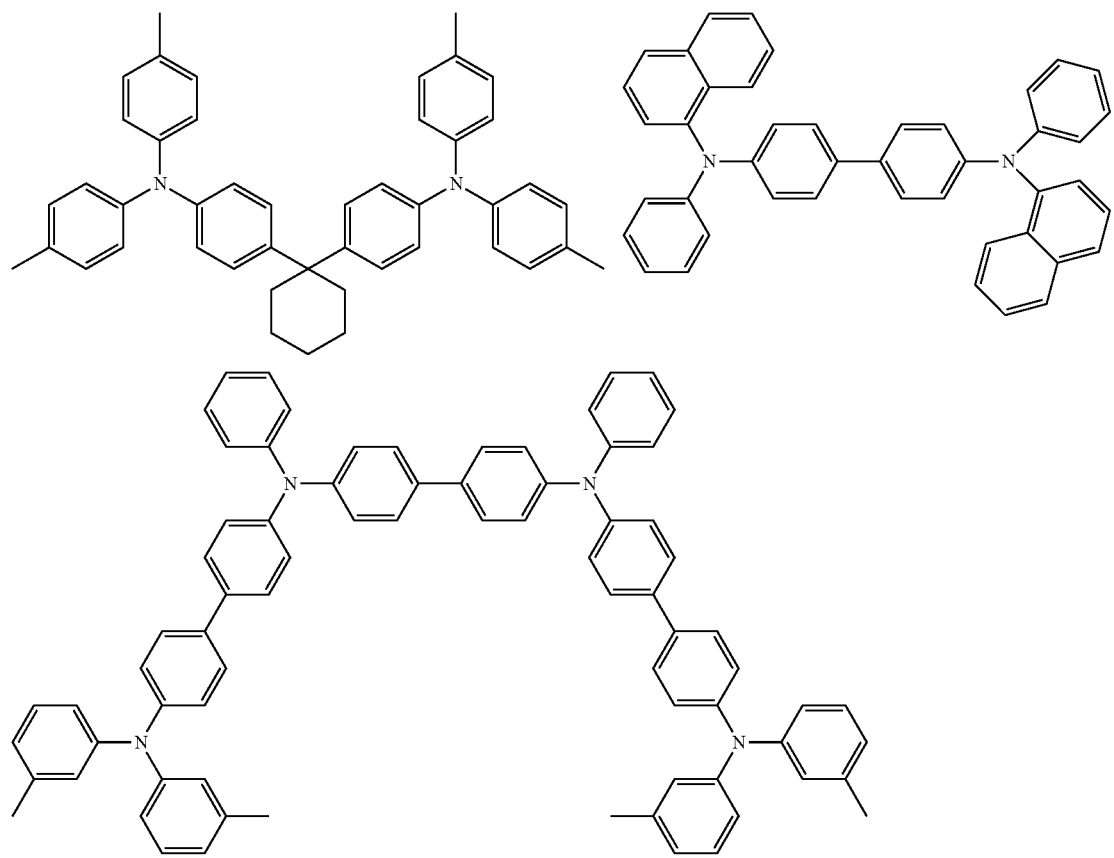

-continued
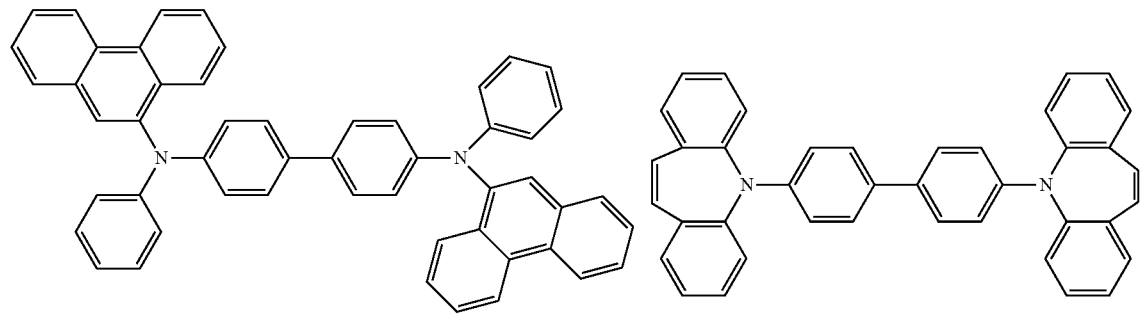
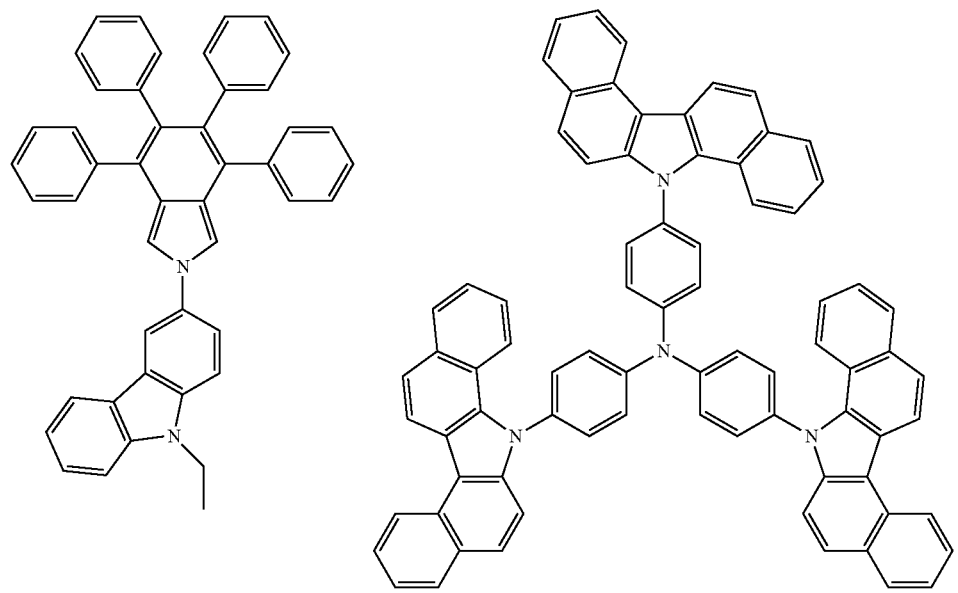
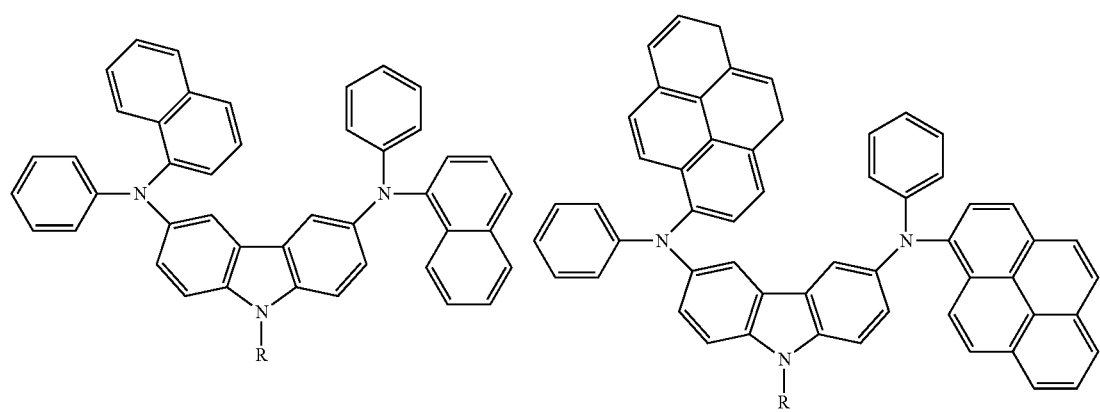

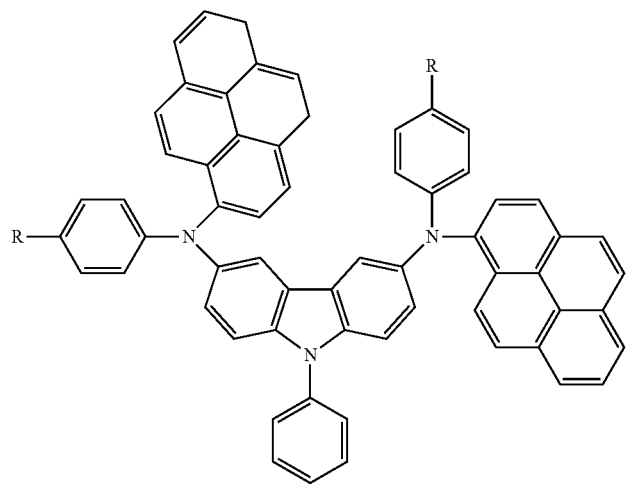
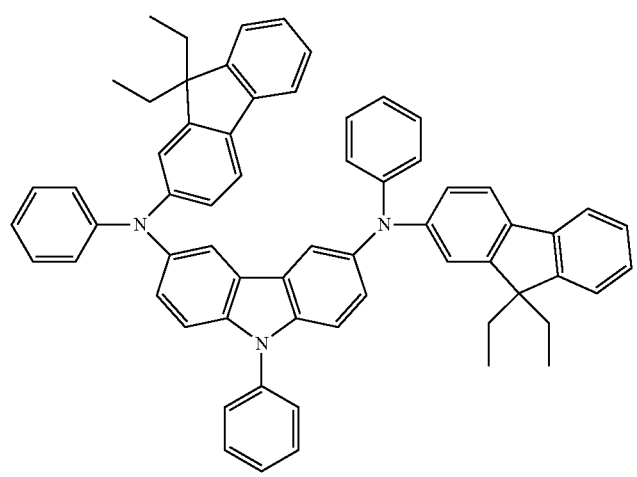
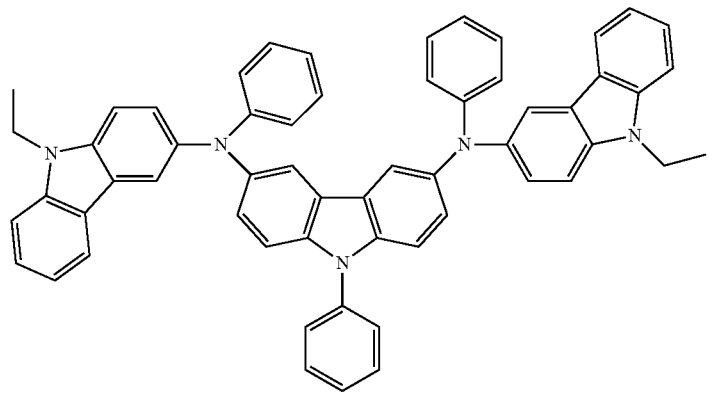

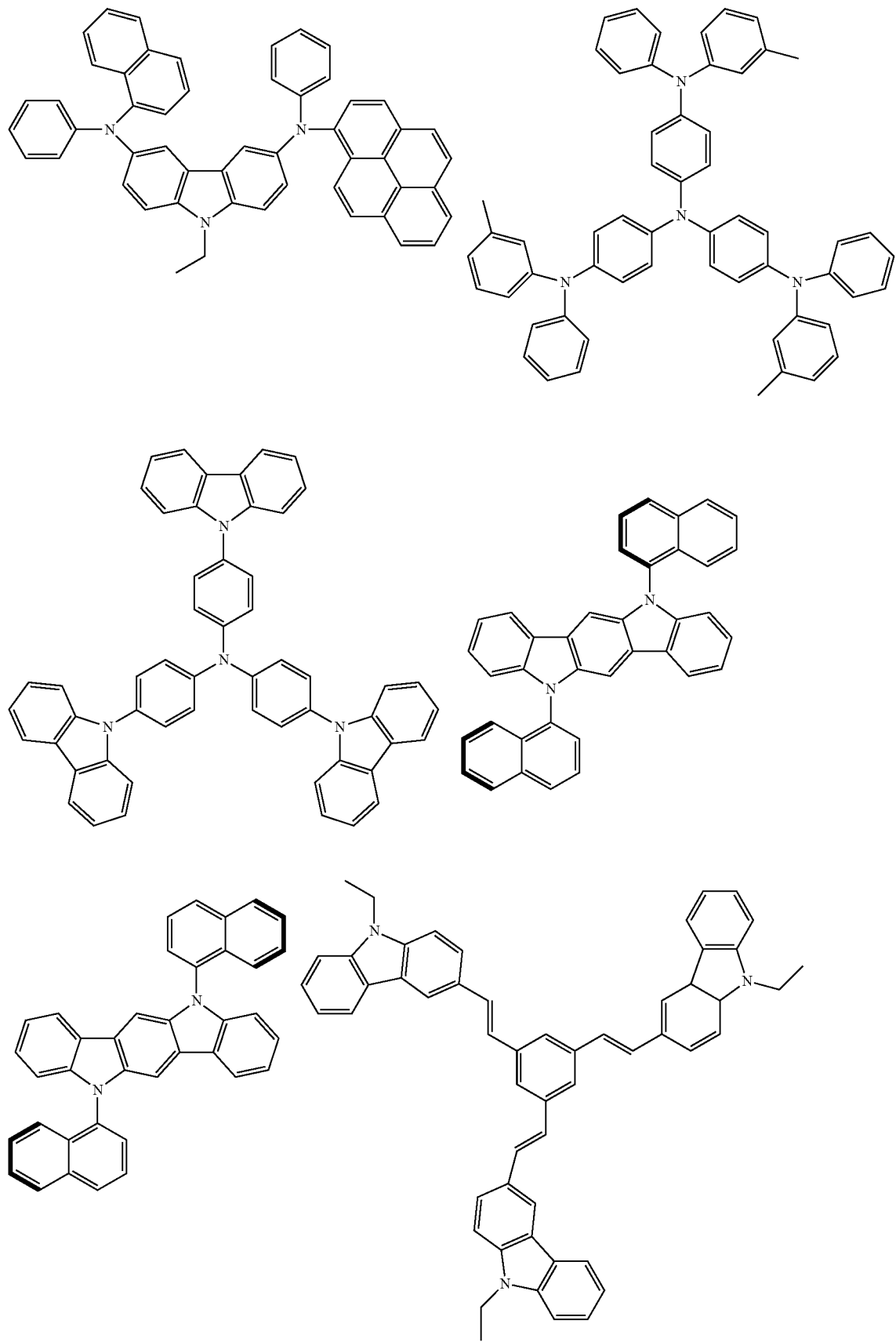

-continued
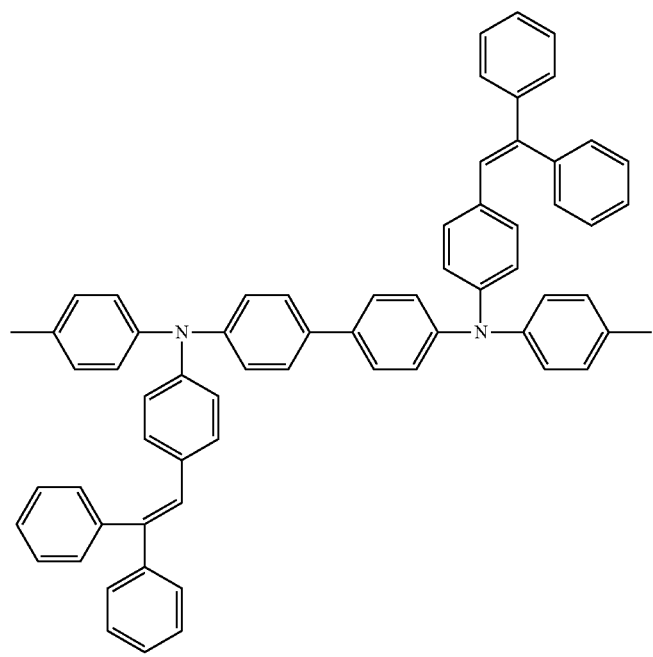
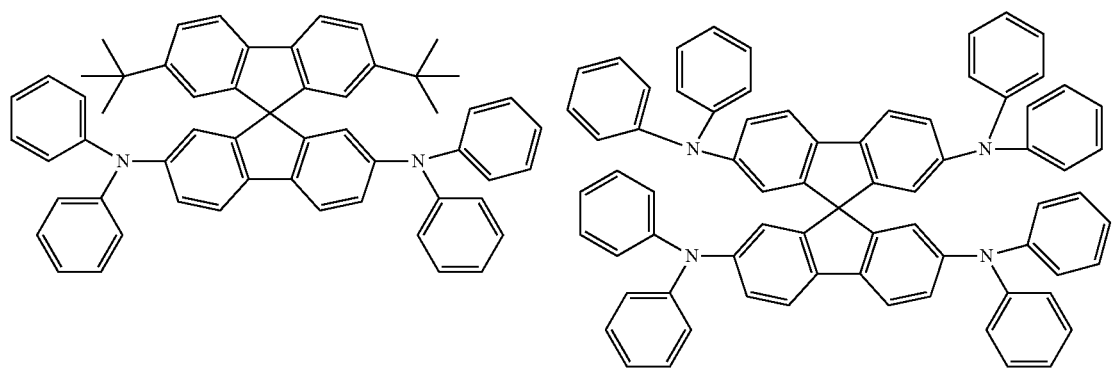
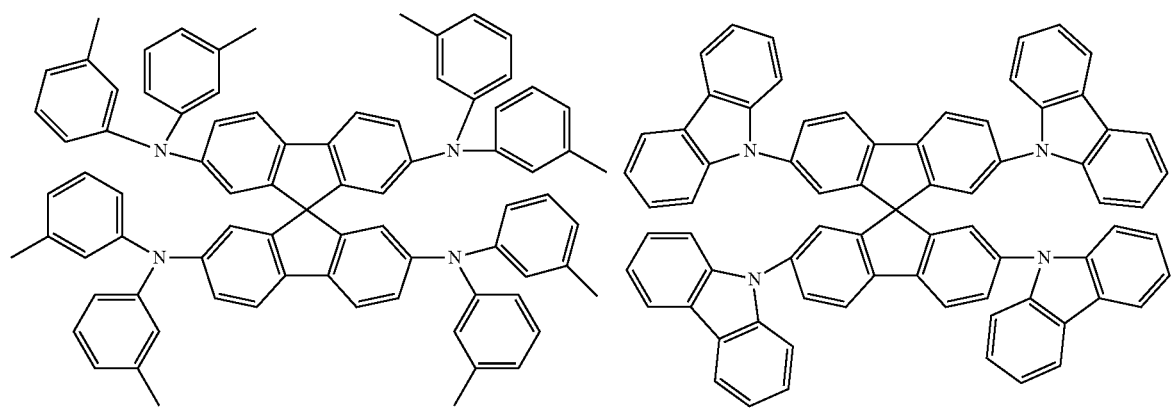
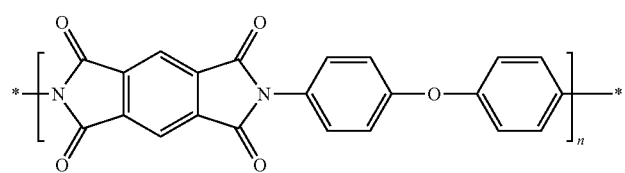

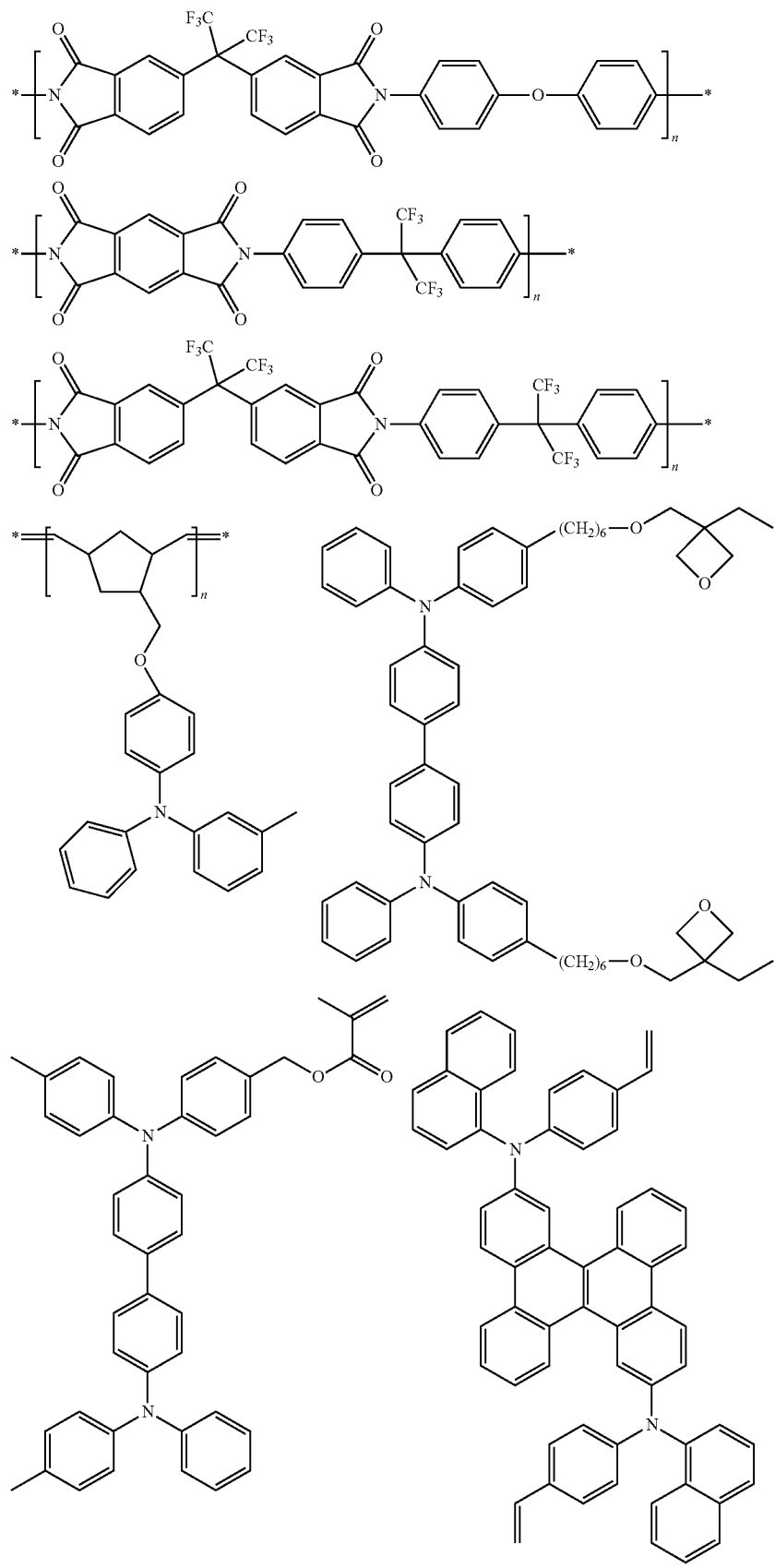

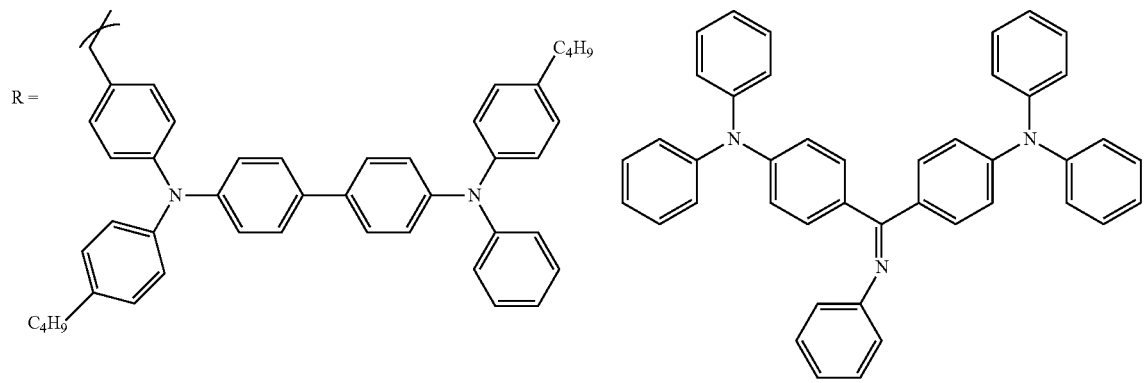
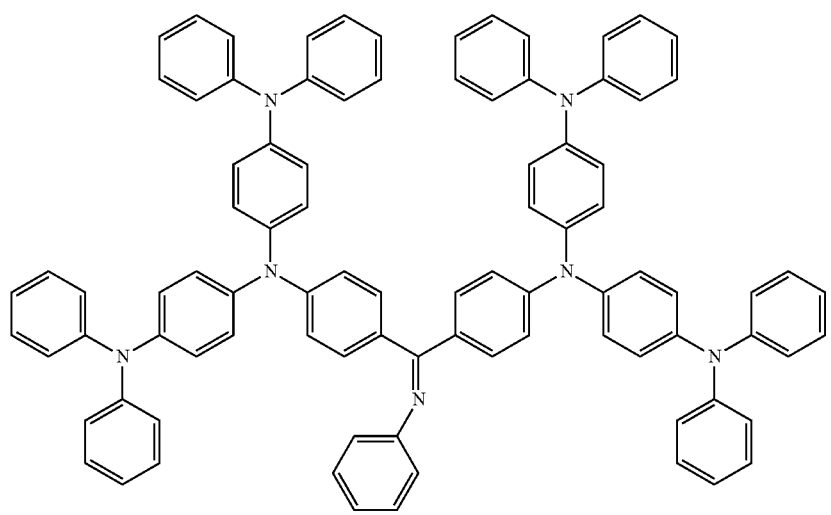
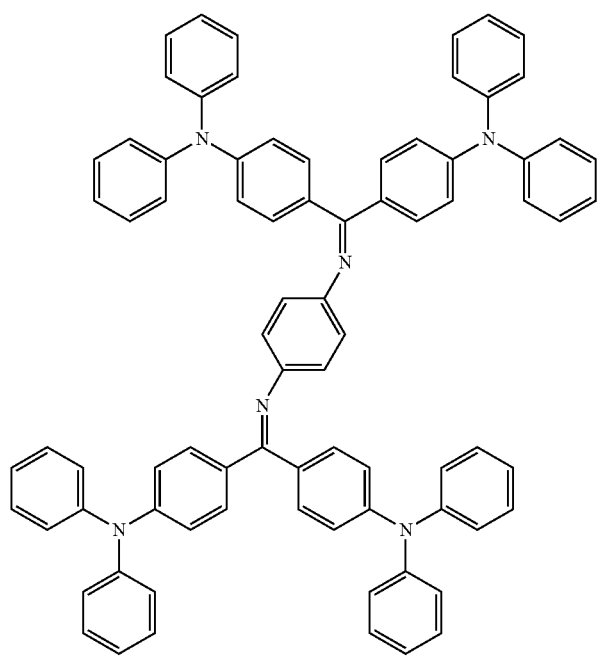

-continued
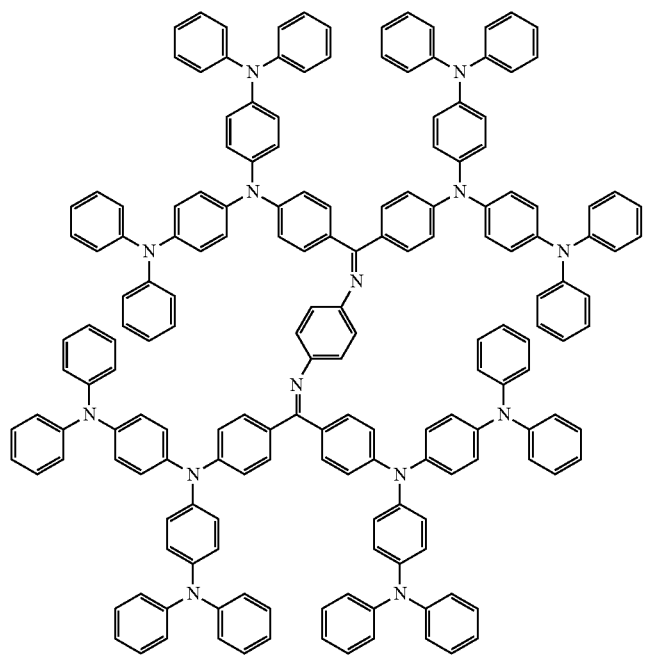
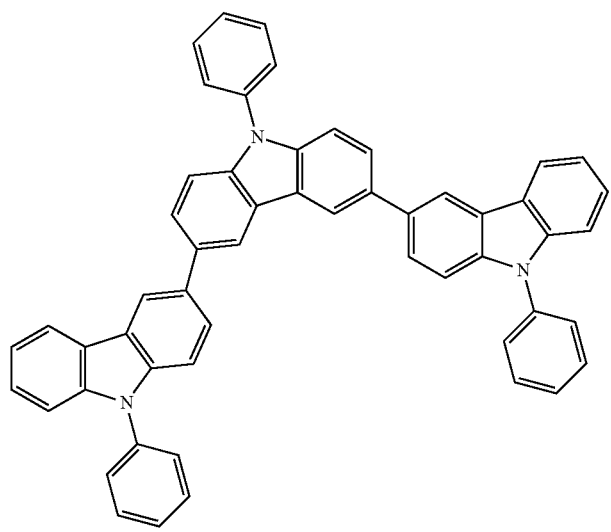
Preferred examples of a compound that may be used as the electron barrier material are shown below.
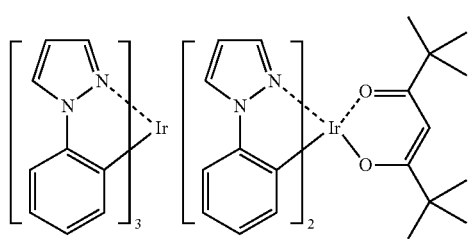
-continued
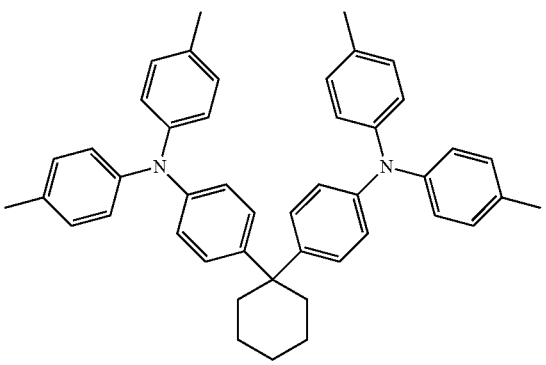

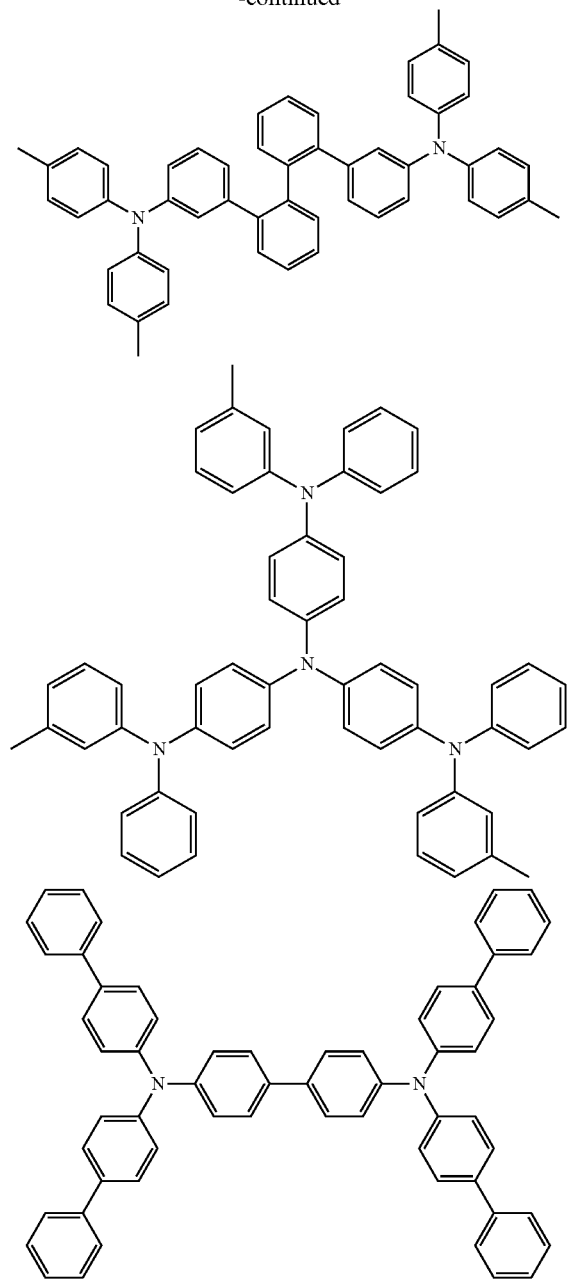
Preferred examples of a compound that may be used as the hole barrier material are shown below.
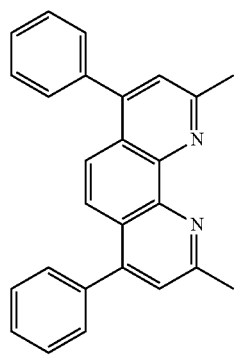
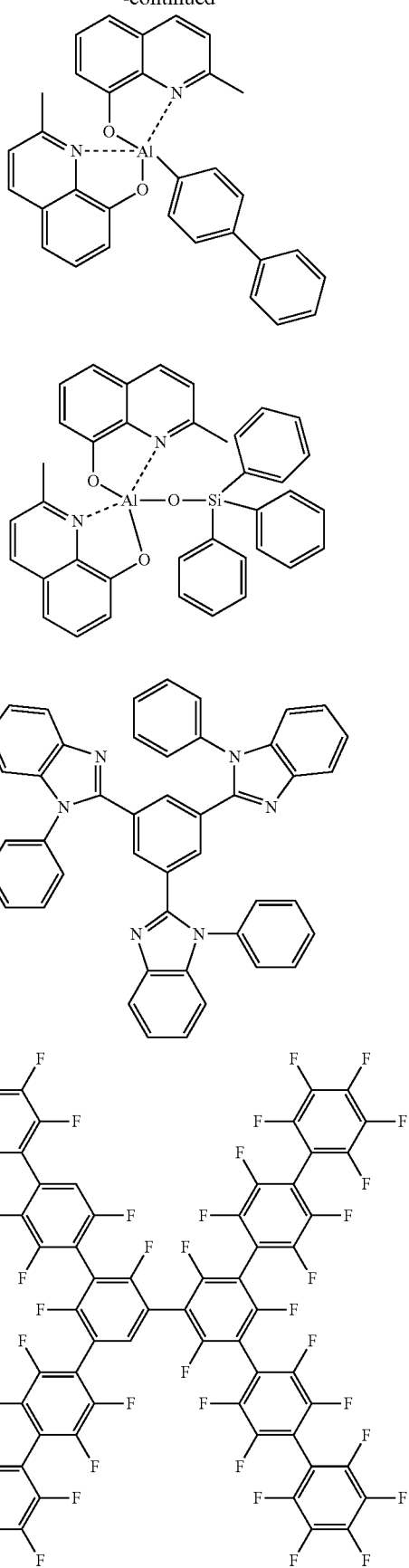

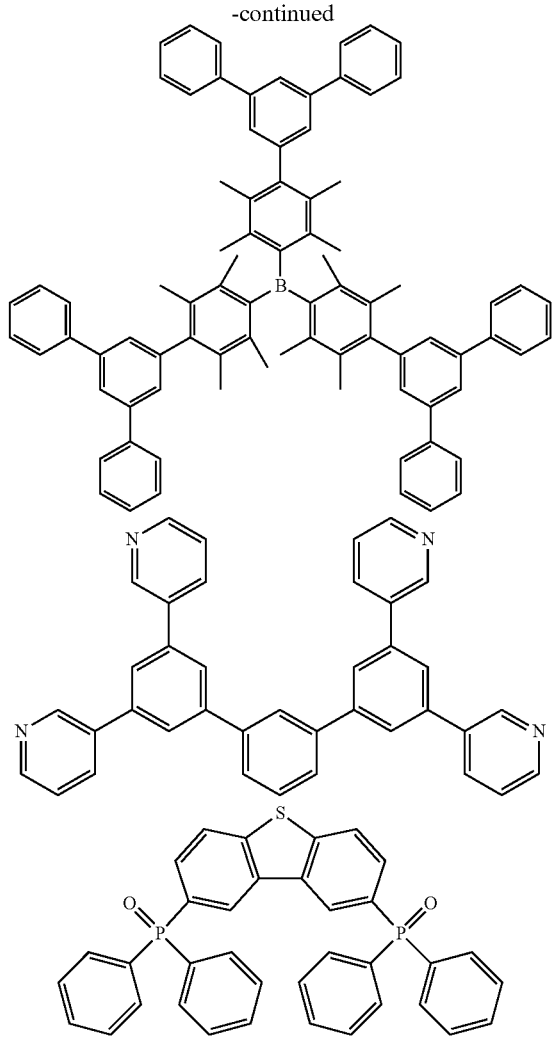
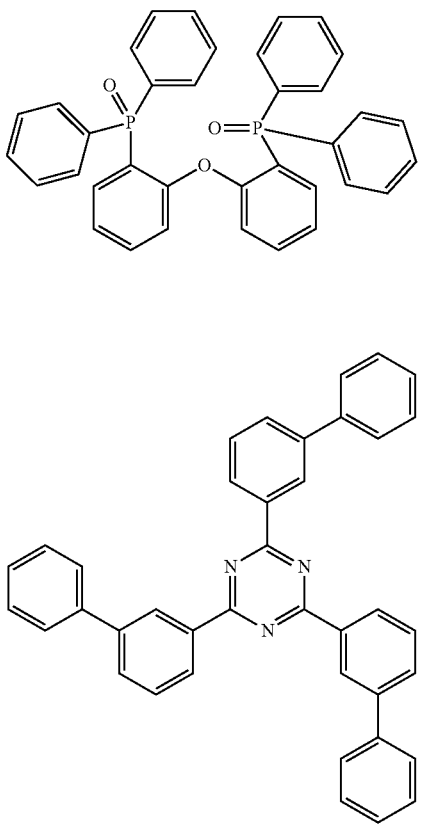
Preferred examples of a compound that may be used as the electron transporting material are shown below.
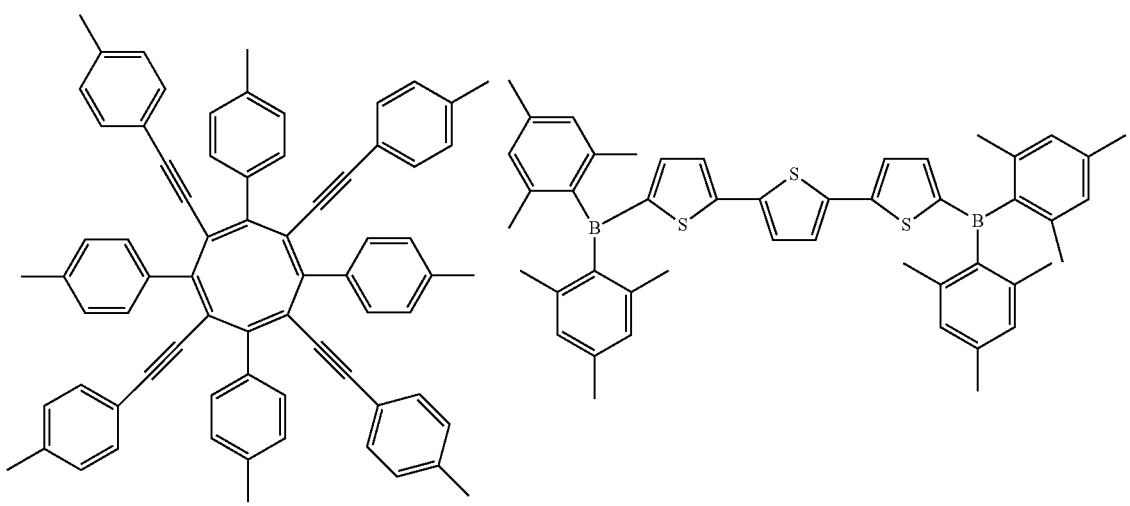

-continued
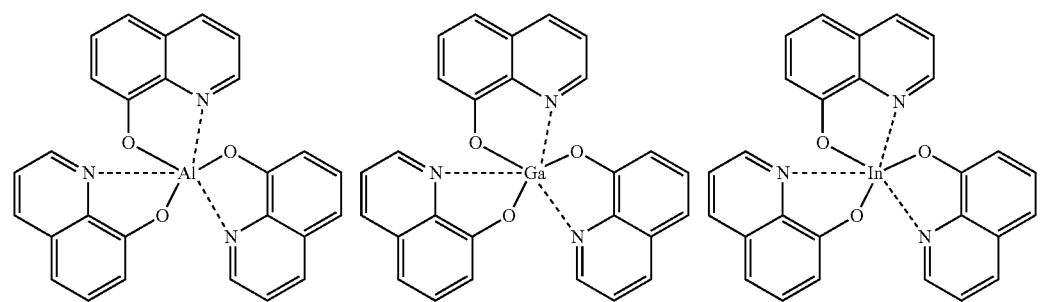
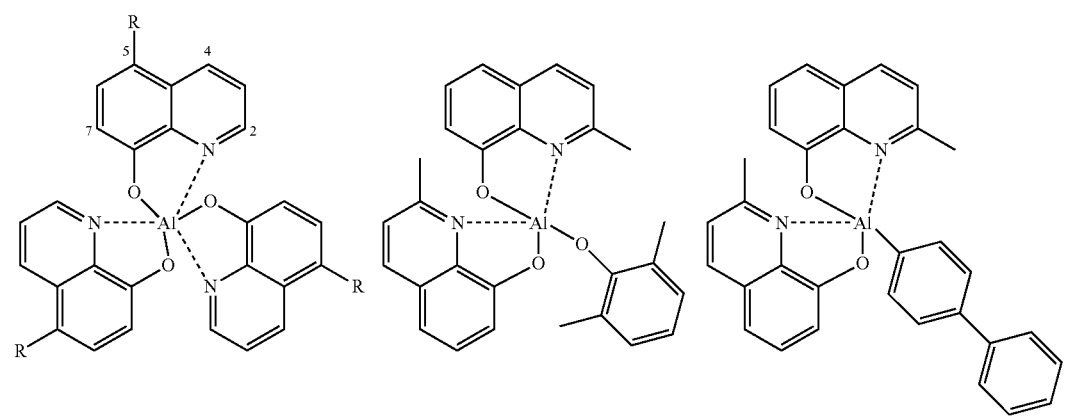
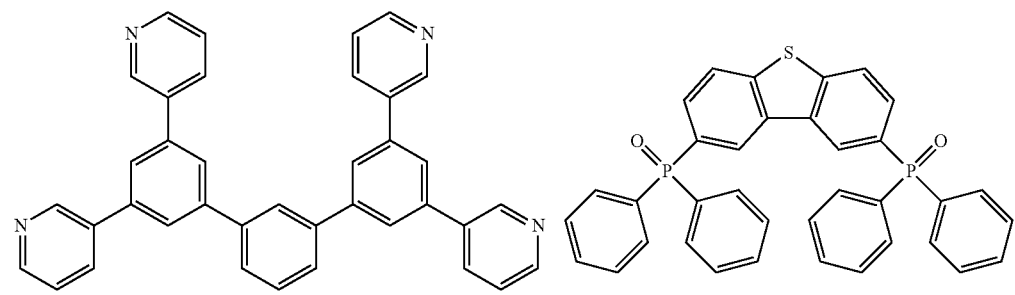
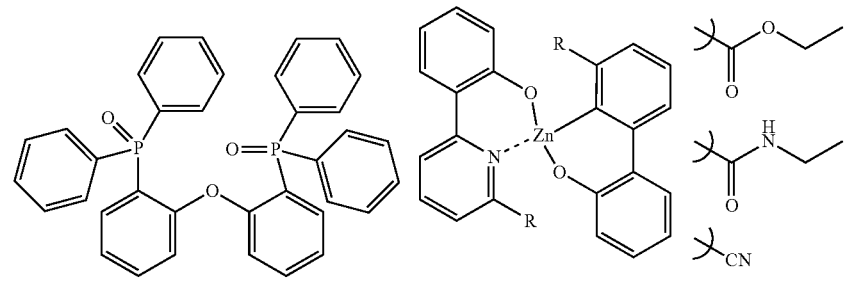
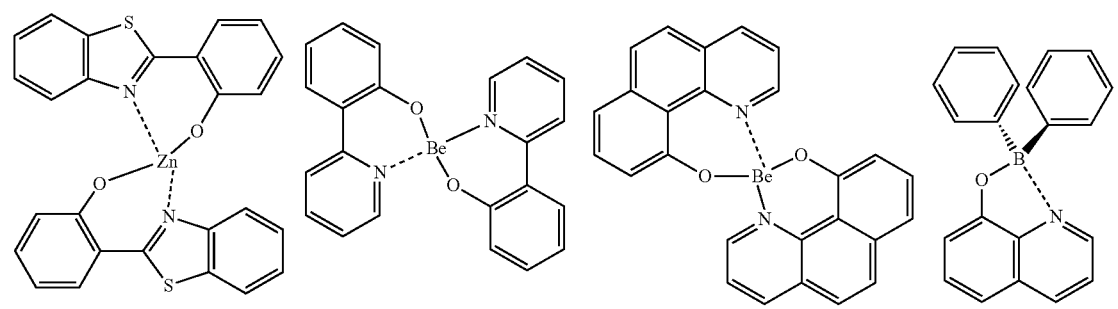

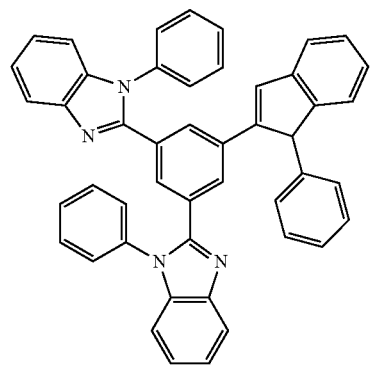
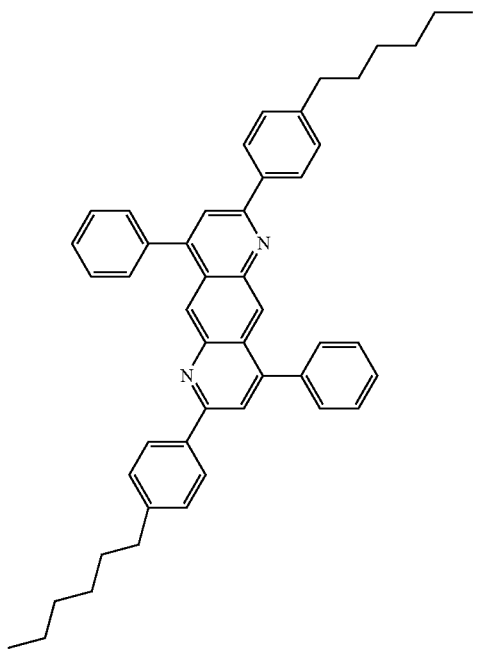
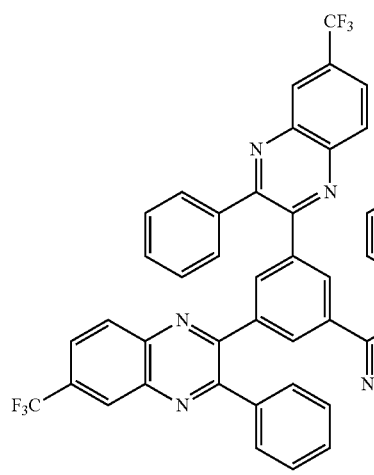
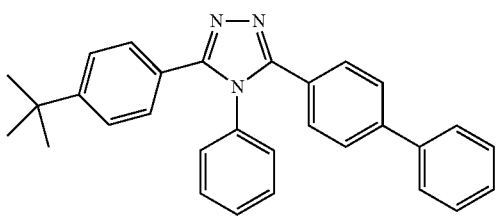
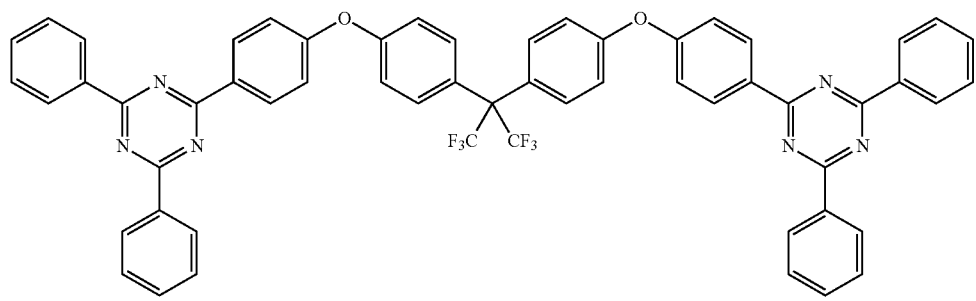

-continued
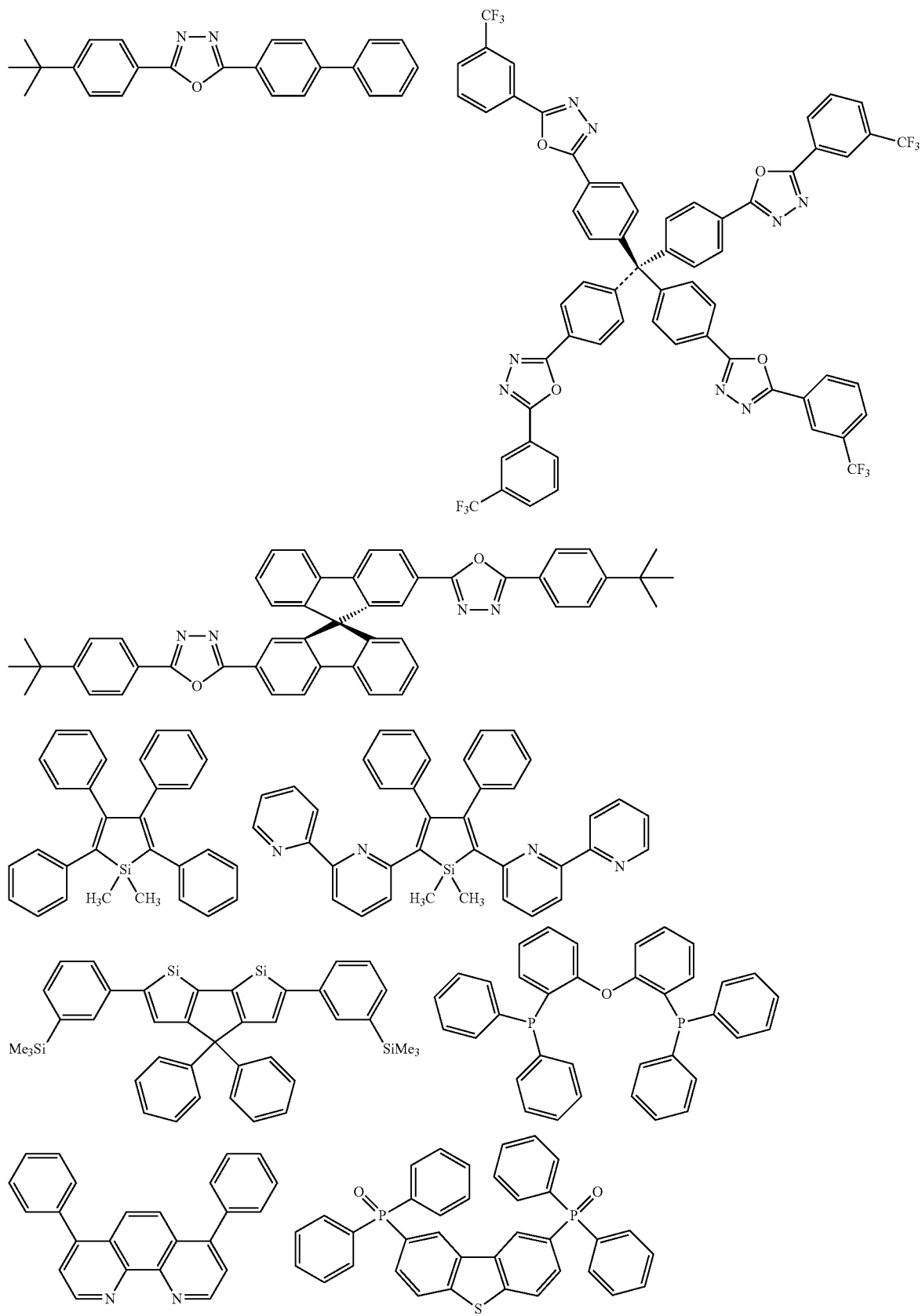

Preferred examples of a compound that may be used as the electron injection material are shown below.

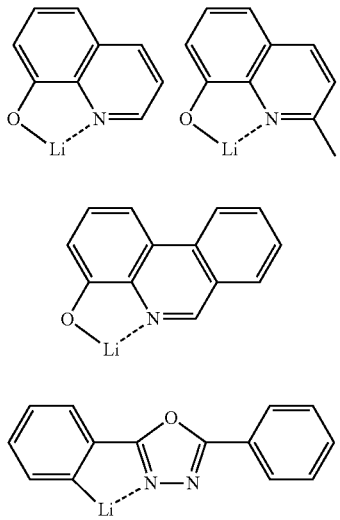

Preferred examples of a compound as a material that may be added are shown below. For example, the compound may be added as a stabilizing material.

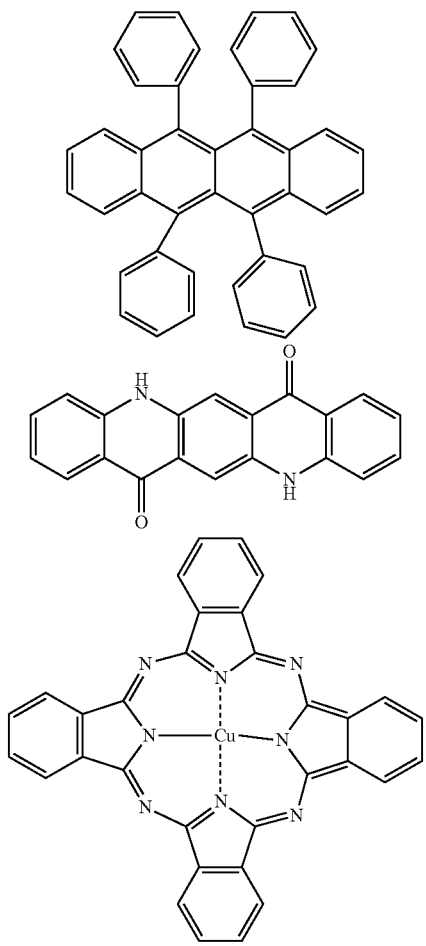

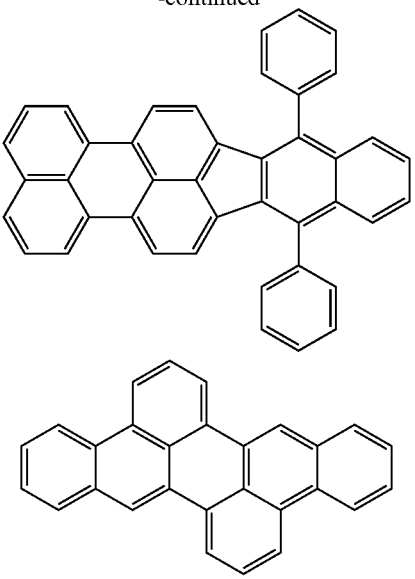

The organic electroluminescent device thus produced by the aforementioned method emits light on application of an electric field between the anode and the cathode of the device. In this case, when the light emission is caused by the excited single energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter fluorescent lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light emitting device that is largely improved in light emission efficiency may be obtained by adding the compound represented by the general formula (1) in the light emitting layer. The organic light emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLES

The features of the invention will be described more specifically with reference to test examples and working examples below. The materials, processes, procedures and the like shown below may be appropriately modified unless they deviate from the substance of the invention. Accordingly, the scope of the invention is not construed as being limited to the specific examples shown below. The light emission characteristics were evaluated by using Semiconductor Parameter Analyzer (E5273A, produced by Agilent Technologies, Inc.), Optical Power Meter (1930C, produced by Newport Corporation), Fiber Optic Spectrometer (USB2000, produced by Ocean Optics, Inc.) and Streak Camera (Model C4334, produced by Hamamatsu Photonics K.K.).

Test Example 1

Evaluation of Thermal Stability

The compound 1, mCP, and the three cyclotriphosphazene compounds having the specific structures described in Non-patent Document 1 (the compounds CP1, CP2 and CP3) were measured for decomposition temperature by measuring the temperature, at which the compound exhibited a weight loss of 5% by weight or more on gradually increasing heating temperature for the compounds. As a result, the compound 1 had a significantly high decomposition temperature of 474° C., but the decomposition temperature of mCP was 55° C. Non-patent Document 1 reports that the cyclotriphosphazene compounds have a decomposition temperature of from 280 to 330° C. Accordingly, it was confirmed that the compound 1 of the invention had significantly high thermal stability.

Test Example 2

Measurement of T1 Level

A methylene chloride solution of the compound 1 (concentration: $10^{-4}$ mol/L) was cooled to 77 K and measured for PL spectrum. The energy of the peak value on the short wavelength end in the PL spectrum was calculated and designated as the T1 level (i.e., the lowest excitation triplet energy level) of the compound. The compound 1 had a T1 level of 3.00 eV (HOMO: 6.48 eV, LUMO: 2.52 eV). Appl. Phys. Lett., 2003, 82, 2422 reports that the T1 level of mCP is 2.9 eV (HOMO: 5.9 eV, LUMO: 2.4 eV).

1. Production and Evaluation of Organic Photoluminescent Device (Thin Film)

Example 1

Figure 2:
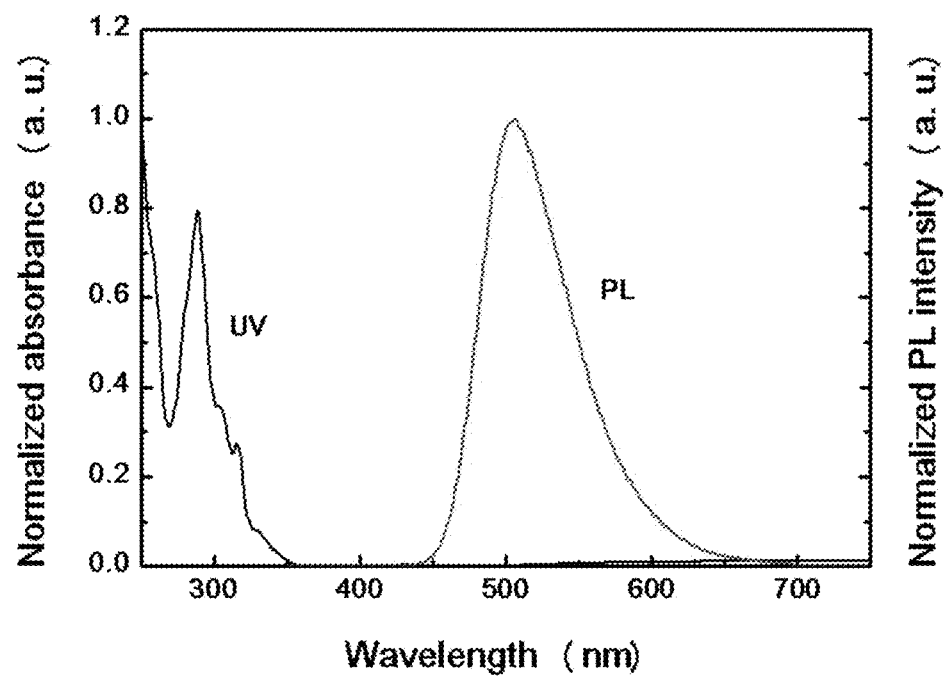
FIG. 2 is the light emission spectrum of the organic photoluminescent device of Example 1.

The compound 1 and 2CzCN were vapor-deposited by a vacuum vapor deposition method from separate vapor deposition sources on a silicon substrate under a condition of a vacuum degree of $5.0 \times 10^{-4}$ Pa, so as to form a thin film having a concentration of 2CzCN of 3.0% by weight to a thickness of 100 nm at a rate of 0.3 nm/sec, thereby providing an organic photoluminescent device. The organic photoluminescent device thus produced was measured for the light emission spectrum with ultraviolet excitation light. The result is shown in FIG. 2. The photoluminescence quantum efficiency was 66.0% in the air and 84.8% in a nitrogen atmosphere.

2. Production and Evaluation of Organic Electroluminescent Device

Example 2

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa or less. Firstly, α-NPD was formed to a thickness of 35 nm on ITO, and thereon mCP was formed to a thickness of 10 nm. Subsequently, the compound 1 and 2CzCN were vapor-co-deposited from separate vapor deposition sources to form a layer having a thickness of 20 nm, which was designated as a light emitting layer. At this time, the concentration of 2CzCN was 3.0% by weight. PPT was then formed to a thickness of 40 nm, then LiF was vacuum vapor-deposited to a thickness of 0.8 nm, and then aluminum (Al) was vapor-deposited to a thickness of 80 nm to form a cathode, thereby producing an organic electroluminescent device.

Figure 3:
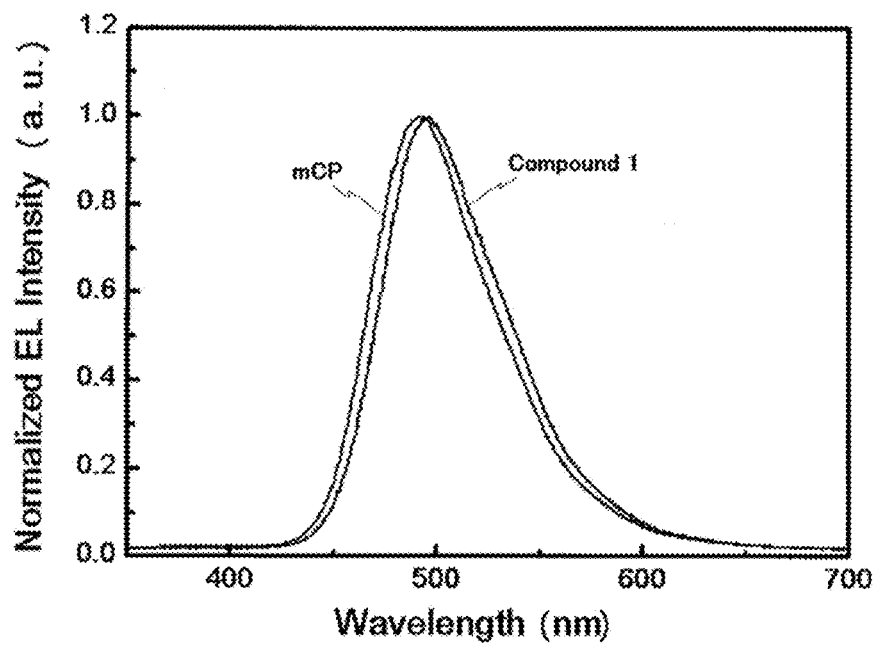
FIG. 3 is the light emission spectra of the organic electroluminescent devices of Example 2 and Comparative Example 1.
Figure 4:
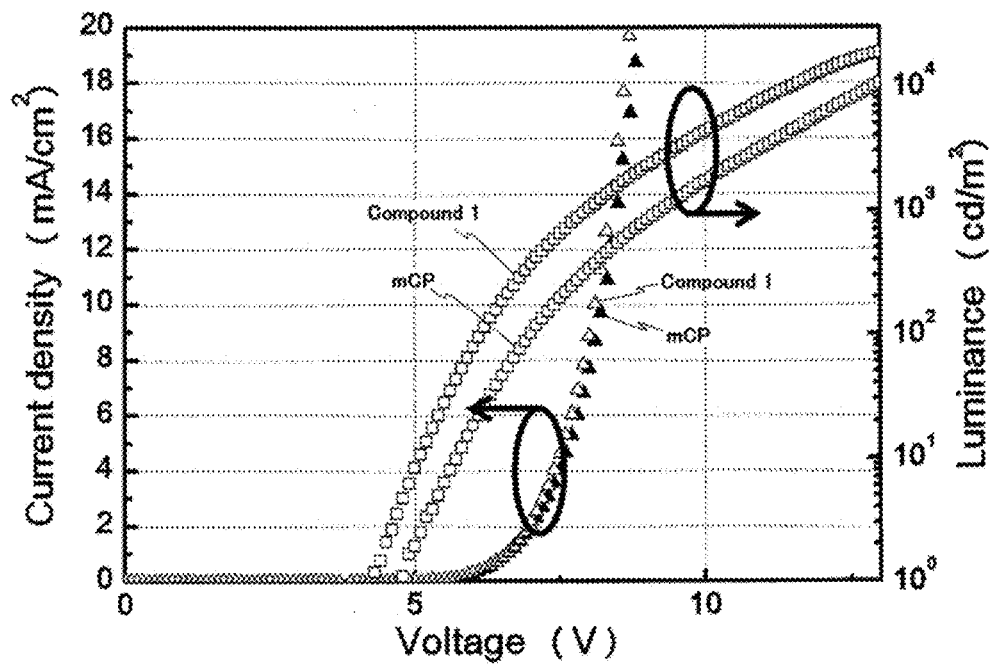
FIG. 4 is a graph showing the electric current density-voltage-luminance characteristics of the organic electroluminescent devices of Example 2 and Comparative Example 1.
Figure 5:
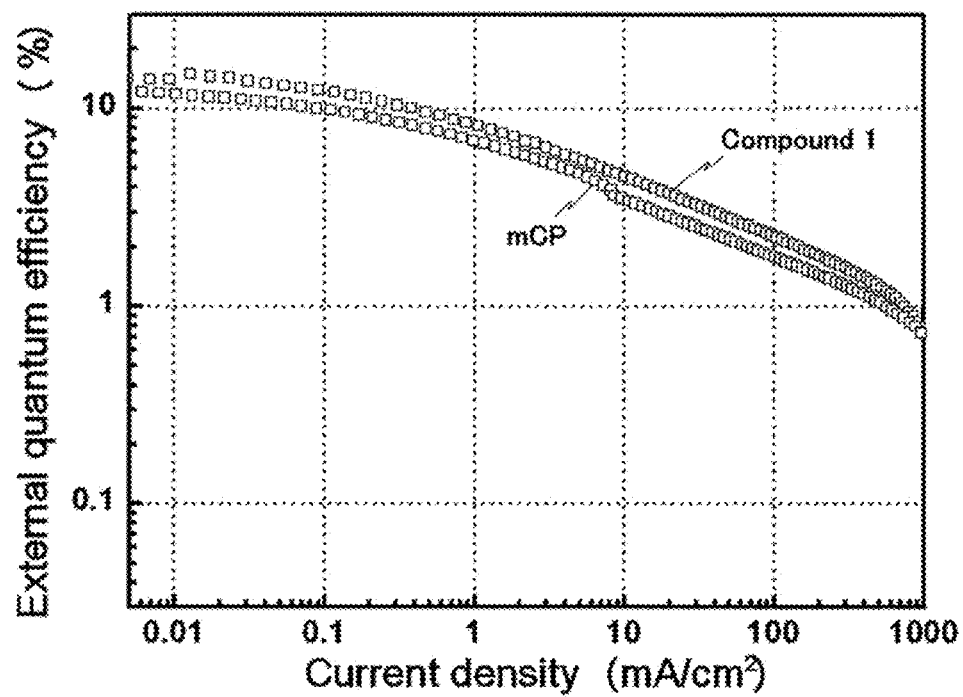
FIG. 5 is a graph showing the electric current density-external quantum efficiency characteristics of the organic electroluminescent devices of Example 2 and Comparative Example 1.

The light emission spectrum of the organic electroluminescent device thus produced is shown in FIG. 3, the electric current density-voltage-luminance characteristics thereof are shown in FIG. 4, and the electric current density-external quantum efficiency characteristics thereof are shown in FIG. 5. The maximum luminance was 18,805 cd/m$^2$, and the external quantum efficiency was 14.9%, which were significantly high. If an ideally balanced organic electroluminescent device is produced with a fluorescent material having a light emission quantum efficiency of 100%, the external quantum efficiency of fluorescent light emission of the device may be from 5 to 7.5% assuming that the light extraction efficiency is from 20 to 30%. It has been ordinarily considered that the value is the theoretical limit value of an external quantum efficiency of an organic electroluminescent device using a fluorescent material. The organic electroluminescent device of the invention using the compound 1 is considerably excellent in such a point that a high external quantum efficiency that exceeds the theoretical limit value is achieved.

Comparative Example 1

An organic electroluminescent device was produced in the same manner as in Example 2 except that mCP was used instead of the compound 1, and evaluated for characteristics in the same manner. The light emission spectrum of the device is shown in FIG. 3, the electric current density-voltage-luminance characteristics thereof are shown in FIG. 4, and the electric current density-external quantum efficiency characteristics thereof are shown in FIG. 5. The maximum luminance was 16,524 cd/m$^2$, and the external quantum efficiency was 11.8%.

It was confirmed that an excellent organic electroluminescent device was provided with the compound 1 rather than mCP.

Comparative Example 2

Figure 6:
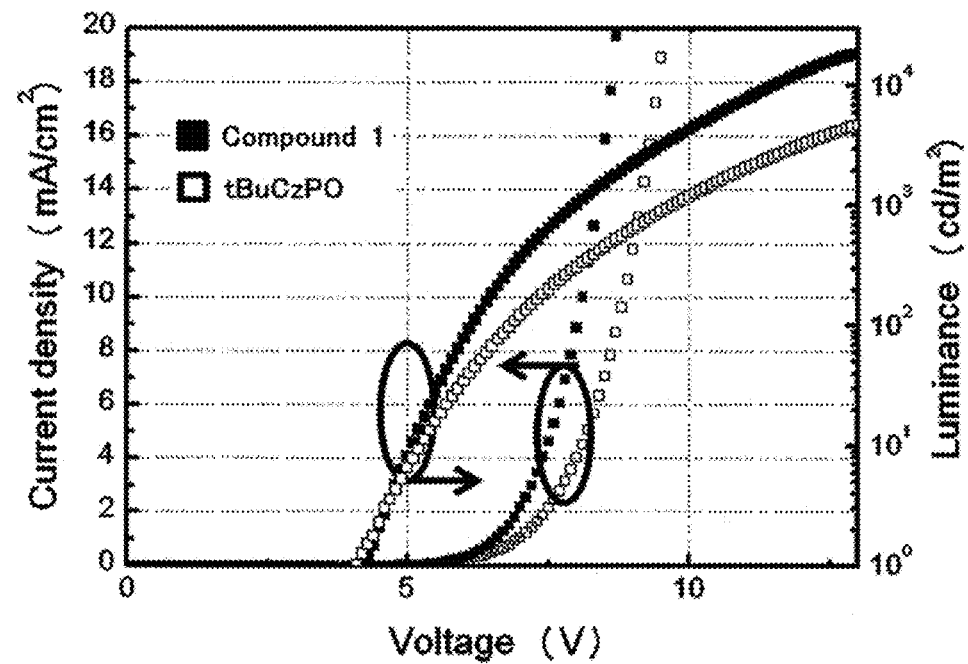
FIG. 6 is a graph showing the electric current density-voltage-luminance characteristics of the organic electroluminescent devices of Example 2 and Comparative Example 2.
Figure 7:
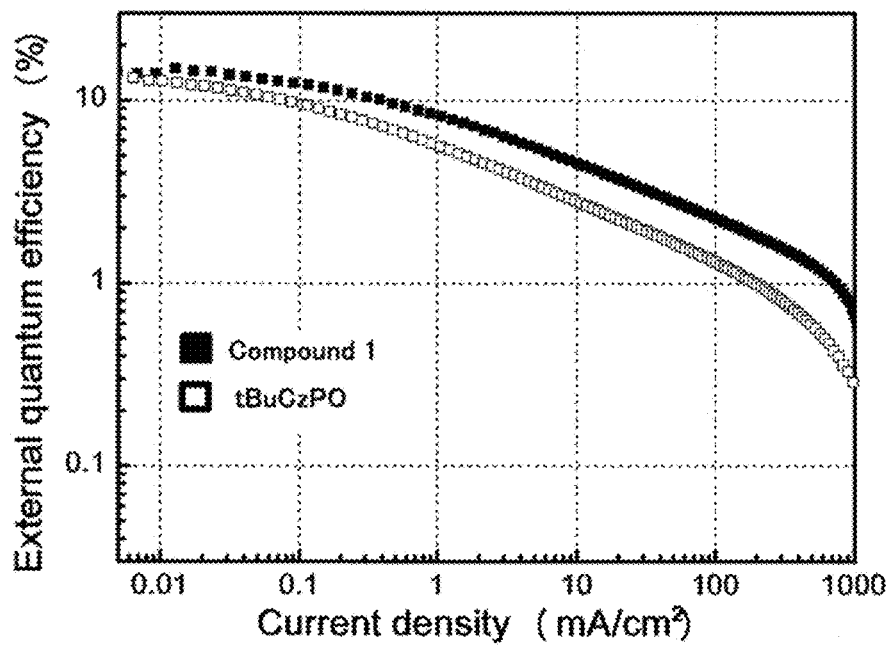
FIG. 7 is a graph showing the electric current density-external quantum efficiency characteristics of the organic electroluminescent devices of Example 2 and Comparative Example 2.

An organic electroluminescent device was produced in the same manner as in Example 2 except that tBuCzPO was used instead of the compound 1, and evaluated for characteristics in the same manner. The electric current density-voltage-luminance characteristics thereof are shown in FIG. 6, and the electric current density-external quantum efficiency characteristics thereof are shown in FIG. 7. The maximum luminance was 6,436 cd/m², and the external quantum efficiency was 12.8%.

It was confirmed that an excellent organic electroluminescent device was provided with the compound 1 rather than tBuCzPO.

Example 3

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa or less. Firstly, α-NPD was formed to a thickness of 35 nm on ITO, and thereon mCP was formed to a thickness of 10 nm. Subsequently, the compound 1 and 4CzIPN were vapor-co-deposited from separate vapor deposition sources to form a layer having a thickness of 20 nm, which was designated as a light emitting layer. At this time, the concentration of 4CzIPN was 3.0% by weight. PPT was then formed to a thickness of 40 nm, then LiF was vacuum vapor-deposited to a thickness of 0.8 nm, and then aluminum (Al) was vapor-deposited to a thickness of 80 nm to form a cathode, thereby producing an organic electroluminescent device.

Figure 8:
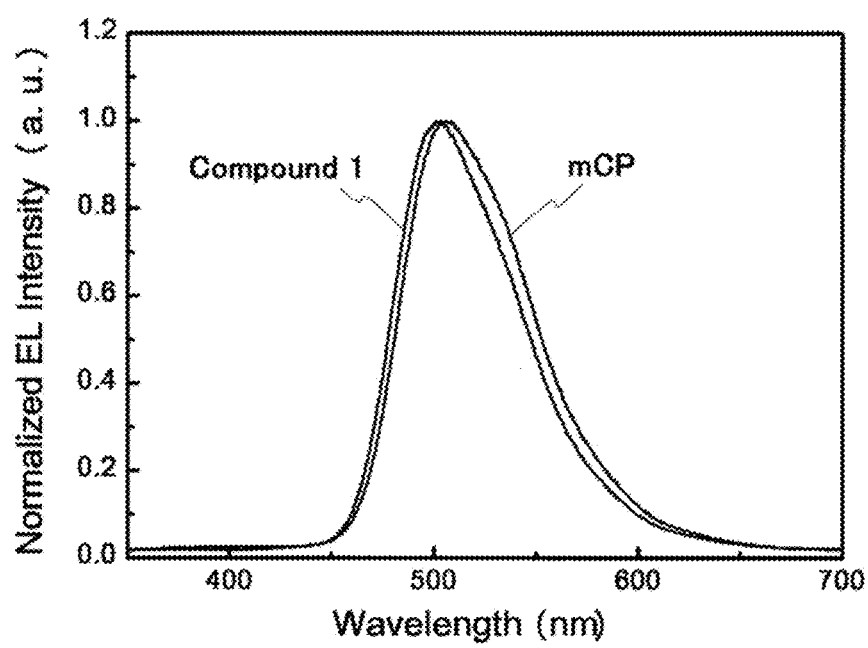
FIG. 8 is the light emission spectra of the organic electroluminescent devices of Example 3 and Comparative Example 3.
Figure 9:
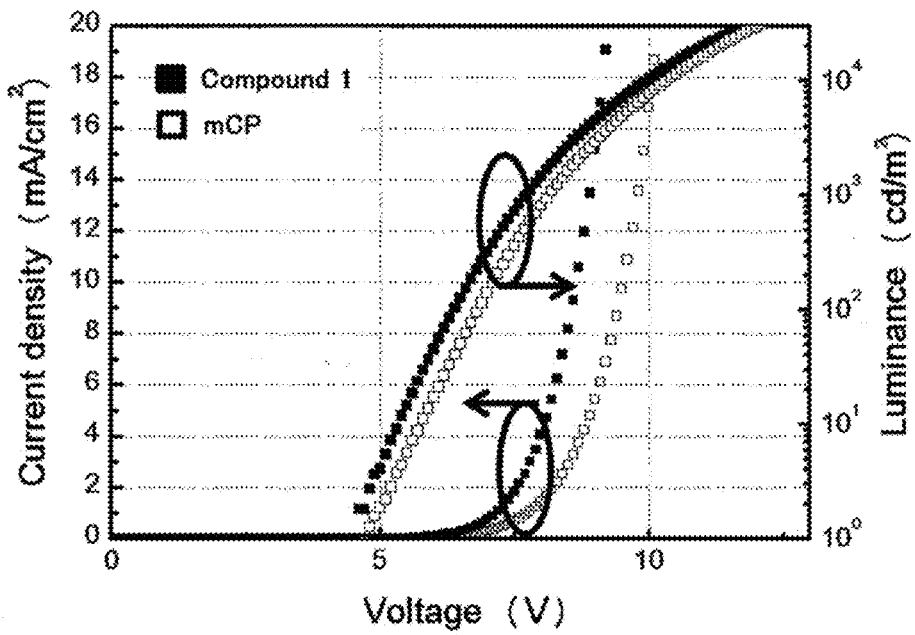
FIG. 9 is a graph showing the electric current density-voltage-luminance characteristics of the organic electroluminescent devices of Example 3 and Comparative Example 3.
Figure 10:
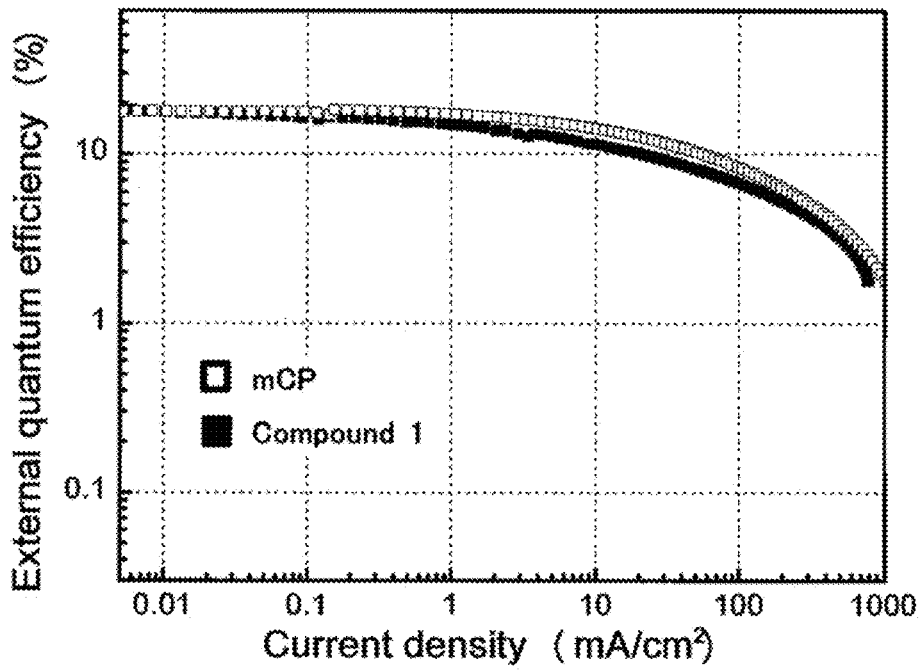
FIG. 10 is a graph showing the electric current density-external quantum efficiency characteristics of the organic electroluminescent devices of Example 3 and Comparative Example 3.

The light emission spectrum of the organic electroluminescent device thus produced is shown in FIG. 8, the electric current density-voltage-luminance characteristics thereof are shown in FIG. 9, and the electric current density-external quantum efficiency characteristics thereof are shown in FIG. 10. The maximum luminance was 54,141 cd/m², and the external quantum efficiency was 17.8%, which were significantly high.

Comparative Example 3

An organic electroluminescent device was produced in the same manner as in Example 3 except that mCP was used instead of the compound 1, and evaluated for characteristics in the same manner. The light emission spectrum of the device is shown in FIG. 8, the electric current density-voltage-luminance characteristics thereof are shown in FIG. 9, and the electric current density-external quantum efficiency characteristics thereof are shown in FIG. 10. The maximum luminance was 49,176 cd/m², and the external quantum efficiency was 17.7%.

It was confirmed that an excellent organic electroluminescent device was provided with the compound 1 rather than mCP.

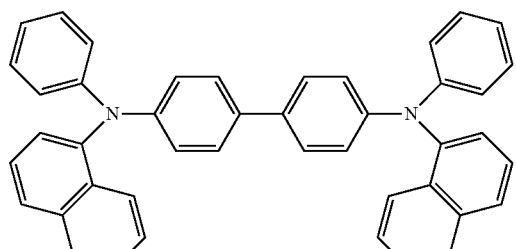

α-NPD

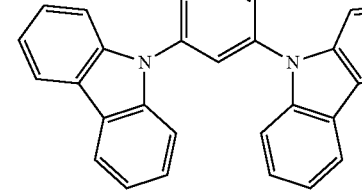

mCP

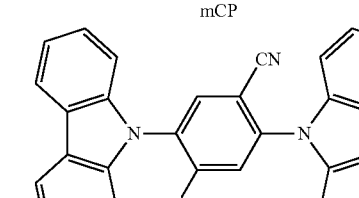

2CzCN

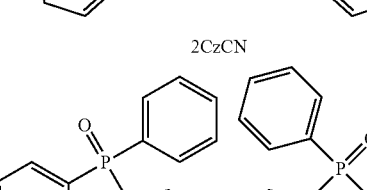

PPT

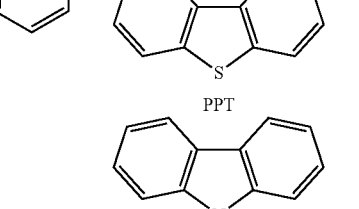

4CzIPN

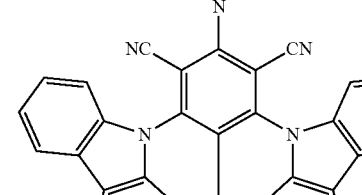

tBuCzPO

INDUSTRIAL APPLICABILITY

The compound represented by the general formula (1) is useful as a charge transporting material. The compound is also useful as a host material in the case where a light emitting material is used as a dopant. Accordingly, an organic light emitting device using the compound represented by the general formula (1) may achieve a high light emission efficiency and a high luminance. Therefore, the invention has high industrial applicability.

REFERENCE SIGNS LIST 1 substrate
2 anode
3 hole injection layer
4 hole transporting layer
5 light emitting layer
6 electron transporting layer
7 cathode

The invention claimed is:

1. A thin film containing a light emitting material and a compound represented by the following formula (1):

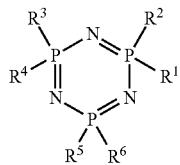

Formula (1)

wherein $R^1$ to $R^6$ each independently represent a group represented by the following formula (2):

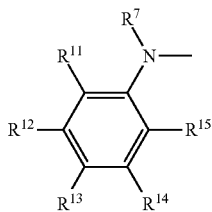

Formula (2)

wherein $R^7$ represents a substituted or unsubstituted aryl group or a substituted or unsubstituted aralkyl group; and $R^{11}$ to $R^{15}$ each independently represent a hydrogen atom or a substituent, and $R^7$ and $R^{11}$, $R^{11}$ and $R^{12}$, $R^{12}$ and $R^{13}$, $R^{13}$ and $R^{14}$, and $R^{14}$ and $R^{15}$ each may be bonded to each other to form a cyclic structure.

2. The thin film according to claim 1, wherein the light emitting material is a blue light emitting material.

3. An organic light emitting device containing an anode, a cathode, and at least one organic layer containing a light-emitting layer between the anode and the cathode, wherein at least one of the organic layers contains a compound represented by the following formula (1):

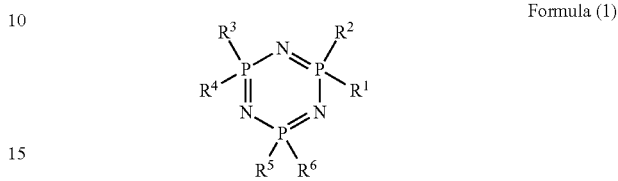

Formula (1)

wherein $R^1$ to $R^6$ each independently represent a group represented by the following formula (2):

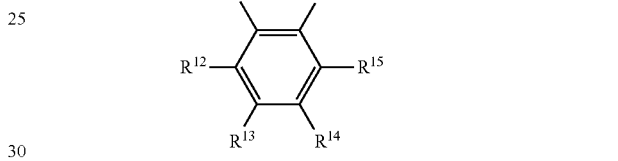

Formula (2)

wherein $R^7$ represents a substituted or unsubstituted aryl group or a substituted or unsubstituted aralkyl group; and $R^{11}$ to $R^{15}$ each independently represent a hydrogen atom or a substituent, and $R^7$ and $R^{11}$, $R^{11}$ and $R^{12}$, $R^{12}$ and $R^{13}$, $R^{13}$ and $R^{14}$, and $R^{14}$ and $R^{15}$ each may be bonded to each other to form a cyclic structure.

4. The organic light emitting device according to claim 3, wherein the charge transporting material is used in a light emitting layer as a host material.

5. The organic light emitting device according to claim 3, wherein the organic light emitting material emits phosphorescent light.

6. The organic light emitting device according to claim 3, wherein the organic light emitting material emits delayed fluorescent light.

7. The organic light emitting device according to claim 3, wherein the organic light emitting device is an organic electroluminescent device.

* * * * *